United States Patent
Fuller et al.

(10) Patent No.: US 10,405,763 B2
(45) Date of Patent: *Sep. 10, 2019

(54) DEVICES AND METHODS FOR NONINVASIVE MEASUREMENT OF INTRACRANIAL PRESSURE

(71) Applicants: Terry A. Fuller, Rydal, PA (US);
William Lai, Philadelphia, PA (US);
Anthony Bellezza, Cherry Hill, NJ (US)

(72) Inventors: Terry A. Fuller, Rydal, PA (US);
William Lai, Philadelphia, PA (US);
Anthony Bellezza, Cherry Hill, NJ (US)

(73) Assignee: Third Eye Diagnostics, Inc., Bethlehem, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/407,505

(22) Filed: Jan. 17, 2017

(65) Prior Publication Data

US 2017/0188860 A1 Jul. 6, 2017

Related U.S. Application Data

(60) Division of application No. 13/804,098, filed on Mar. 14, 2013, now Pat. No. 9,585,578, which is a
(Continued)

(51) Int. Cl.
*A61B 5/03* (2006.01)
*A61B 5/00* (2006.01)
(Continued)

(52) U.S. Cl.
CPC .............. *A61B 5/031* (2013.01); *A61B 3/16* (2013.01); *A61B 5/6821* (2013.01); *A61B 8/10* (2013.01);
(Continued)

(58) Field of Classification Search
CPC ........... A61B 3/16; A61B 3/165; A61B 5/031; A61B 5/6821; A61B 5/5223
See application file for complete search history.

(56) References Cited

U.S. PATENT DOCUMENTS 3,446,061 A 5/1969 Draeger et al.
3,706,304 A 12/1972 Sisler
(Continued)

OTHER PUBLICATIONS

Echegaray et al., "Automated Analysis of Optic Nerve Images for Detection and Staging of Papilledema", Invest Ophthalmol Vis Sci, 2011, 52(10), 7470-7478.
(Continued)

*Primary Examiner* — Adam J Eiseman
(74) *Attorney, Agent, or Firm* — BakerHostetler LLP

(57) ABSTRACT

Provided are systems and methods for noninvasively assessing intracranial pressure by controllably osculating at least a portion of a subject's ocular globe while applying a force sufficient to collapse an intraocular blood vessel and correlating the collapse pressure to intracranial pressure. Also provided are ophthalmic components useful in ophthalmic imaging applications, such as retinal, corneal, and pupil imaging. The components may include an optical contact surface that has a radius of curvature that is greater than the radius of curvature of a subject's cornea.

5 Claims, 21 Drawing Sheets

Related U.S. Application Data continuation-in-part of application No. 13/309,920, filed on Dec. 2, 2011, now Pat. No. 9,078,612.

(51) Int. Cl.
*A61B 3/16* (2006.01)
*A61B 8/10* (2006.01)
*A61B 8/00* (2006.01)
*A61B 8/08* (2006.01)
*A61B 3/00* (2006.01)

(52) U.S. Cl.
CPC ............ *A61B 8/4218* (2013.01); *A61B 8/488* (2013.01); *A61B 8/5223* (2013.01); *A61B 3/0066* (2013.01)

(56) References Cited

U.S. PATENT DOCUMENTS

| | | | |
|---|---|---|---|
| 3,832,891 A | | 9/1974 | Stuckey |
| 3,977,237 A | | 8/1976 | Tesi |
| 4,523,597 A | | 6/1985 | Sawa et al. |
| 4,628,938 A | * | 12/1986 | Lee ................ A61B 3/16 600/405 |
| 5,070,875 A | | 12/1991 | Falck et al. |
| 5,355,884 A | | 10/1994 | Bennett |
| 5,439,001 A | | 8/1995 | Butterfield et al. |
| 6,083,160 A | | 7/2000 | Lipman |
| 6,093,147 A | | 7/2000 | Kontiola |
| 6,129,682 A | | 10/2000 | Borchert et al. |
| 6,179,779 B1 | | 1/2001 | Falck et al. |
| 6,394,968 B1 | | 5/2002 | Wallace |
| 6,413,214 B1 | | 7/2002 | Yang |
| 6,471,647 B2 | | 10/2002 | Falck et al. |
| 6,589,189 B2 | | 7/2003 | Meyerson et al. |
| 6,706,001 B2 | | 3/2004 | Fresco |
| 6,736,778 B2 | | 5/2004 | Falck, Jr. et al. |
| 6,776,756 B2 | | 8/2004 | Feldon et al. |
| 6,939,299 B1 | | 9/2005 | Petersen et al. |
| 7,037,267 B1 | | 5/2006 | Lipson et al. |
| 7,122,007 B2 | | 10/2006 | Querfurth |
| 7,153,267 B2 | | 12/2006 | Falck, Jr. et al. |
| 8,317,701 B2 | * | 11/2012 | Livne ................ A61B 3/16 600/398 |
| 9,398,861 B2 | | 7/2016 | Bellezza et al. |
| 2002/0049389 A1 | | 4/2002 | Abreu |
| 2004/0230124 A1 | | 11/2004 | Querfurth |
| 2005/0020896 A1 | | 1/2005 | Fuller et al. |
| 2006/0206037 A1 | * | 9/2006 | Braxton ................ A61B 3/12 600/561 |
| 2006/0217611 A1 | | 9/2006 | Falck et al. |
| 2006/0235313 A1 | | 10/2006 | Falck et al. |
| 2007/0123769 A1 | | 5/2007 | Fuller et al. |
| 2007/0173713 A1 | | 7/2007 | Falck et al. |
| 2008/0077000 A1 | | 3/2008 | Falck et al. |

OTHER PUBLICATIONS

Eisenlohr et al., "Manometric Studies of the Pressure-Volume Relationship in Living and Enucleated Eyes of Individual Human Subjects", Brit J. Ophthal., 1962, 46, 536-548.

Kimberly et al., "Correlation of Optic Nerve Sheath Diameter with Direct Measurement of Intracranial Pressure", Society for Academic Emergency Medicine, 2008, 15(2), 201-204.

Querfurth et al, "Prediction of Intracranial Pressure From Noninvasive Transocular Venous and Arterial Hemodynamic Measurements", Neurocritical Care, 2004, 1(2),183-194.

Querfurth et al, "Ophthalmodynamometry for ICP Prediction and Pilot Test on Mt. Everest" BMC Neurology, Nov. 2010, 10:106.

* cited by examiner

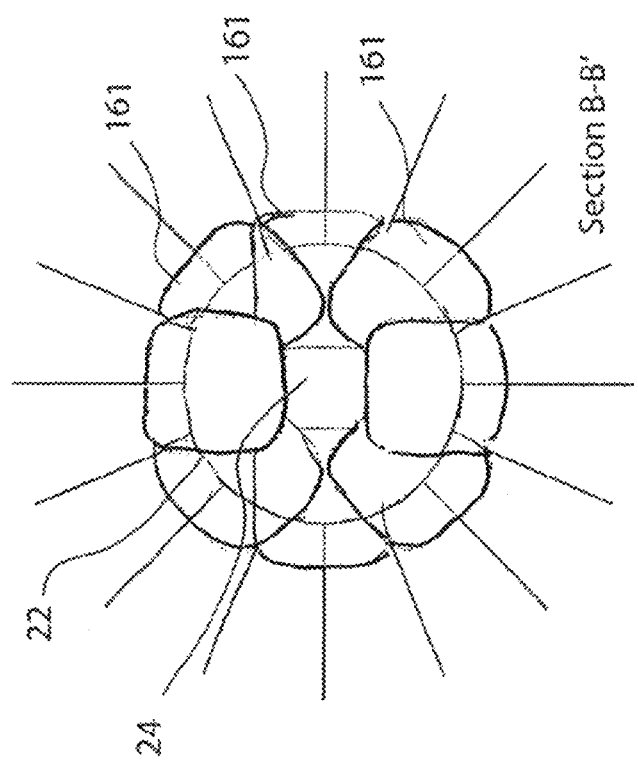

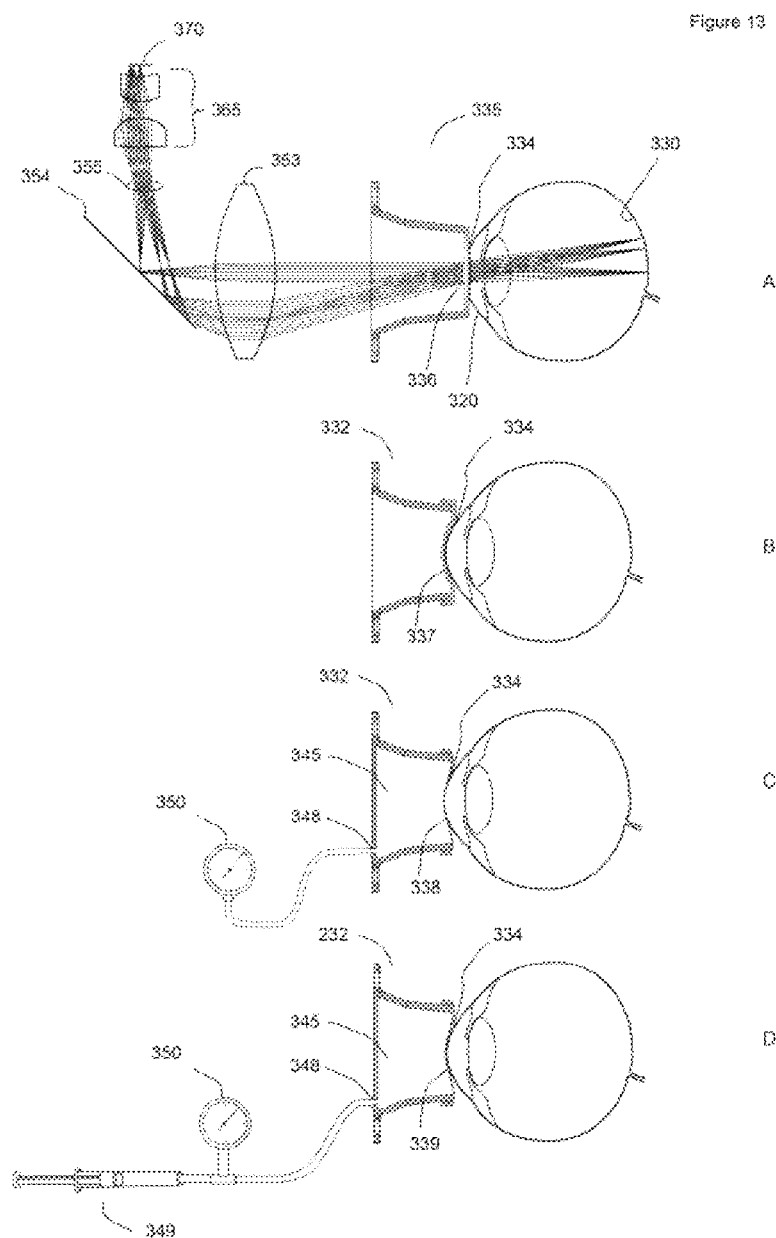

DEVICES AND METHODS FOR NONINVASIVE MEASUREMENT OF INTRACRANIAL PRESSURE

RELATED APPLICATIONS

The present application is a divisional of now-allowed U.S. patent application Ser. No. 13/804,098, "Devices and Methods for Noninvasive Measurement of Intracranial Pressure," filed Mar. 14, 2013, which is a continuation-in-part of U.S. patent application Ser. No. 13/309,920, "Devices and Methods for Noninvasive Measure of Intracranial Pressure," filed on Dec. 2, 2011, and issued as U.S. Pat. No. 9,078,612. The entireties of the foregoing applications are incorporated herein by reference for any and all purposes.

TECHNICAL FIELD

The present disclosure relates to the field of neurological instrumentation and more specifically to the field of measuring intracranial pressure.

BACKGROUND

Intracranial pressure (ICP) is measured for the diagnosis and the management of disorders such as hydrocephalus and pseudotumor cerebri. ICP is often measured following serious head injury, stroke edema, and intracranial hemorrhage, and is also of value in the management of certain neurological or ophthalmic diseases that are associated with increased cerebral pressure.

The current standard of care to measure ICP involves surgically inserting a sensor into the cranium through an access hole drilled through the skull. Present treatment techniques for monitoring ICP or managing intracranial hypertension (ICH) generally require invasive placement of subarachnoid bolts, counter-pressure epidural devices (Ladd or Camino fiber-optic monitors) or intra-ventricular catheters coupled to external pressure monitors. Such surgical procedures carry the risk of complications including infections, hemorrhage, herniation, damage to nervous tissue, and death, and are very expensive. In addition, cerebrospinal fluid pressure may be altered the instant the measurement is performed as a result of leakage of cerebrospinal fluid. Despite the risks, invasive measurements of ICP are nonetheless commonplace, as they provide a treatment option in addition to a diagnostic option, which non-invasive devices cannot.

Because of these risks, ICP is only measured in patients who are critically ill and is not a practical solution for assessing the severity of a patient's injury or in triage. Accordingly, there is a need for non-invasive, momentary assessment of ICP in certain acute situations such as patients with acute shunt obstruction, in the neuro-intensive care unit (NICU) when lumbar puncture is not practical, in the emergency room or by emergency medical technicians (EMT) and other civilian and military first-responders in response to head injury or the like.

Existing attempts to accurately and non-invasively determine ICP are not optimal, as such approaches do not provide a reliable measure of ICP. Individual baseline variability due in part to anatomical variances further limits the application of these methods. Additionally, these methods have demonstrated insufficient precision when compared to invasive ICP monitors. Accordingly, there is an unmet need in the art for easy to use, portable and inexpensive devices and methods capable of non-invasive determination of intracranial pressure.

Part of a routine neurologic assessment in patients with a head injury or when elevated ICP is suspected is the pupillary reflex examination. The pupillary reflex is the response of the pupil to light and can provide valuable information about the degree or progression of brain injury. It has been shown that patients with an abnormal pupil response also have significantly higher ICP than patients with normal pupillary activity.

Traditionally, the pupillary reflex has been subjective and determined by waving a flashlight into a patient's eye to observe the pupil's reactivity and thus the status of the nervous system and brain. Devices to quantitatively assessed changes in constriction and dilatation of pupils in response to light also exist. Such devices are expensive, serve the single function, require additional training and are not integrated into a system for determining ICP.

Accordingly, there is an unmet need in the art for a method and integrated instrument to measure, in a virtually simultaneous or sequential manner, a spectrum of neurological and neuro-ophthalmic indicators such as ICP, ophthalmodynamometry (ODM), IOP, pupillary reflex and other similar functions. Such an instrument would significantly enhance the available information to assess the neurological status of the patient.

In addition to the patient conditions summarized above in which an assessment of ICP is desirable, the field would also benefit from devices and methods capable of providing a more accurate diagnosis of glaucoma. Traditionally, a patient's intraocular pressure (IOP) has been to the single most important metric that determines a patient's susceptibility to glaucoma. Knowledge of a patient's ICP in addition to a patient's IOP will provide the clinician with the translaminar pressure (i.e., the pressure difference between IOP and ICP that is applied to the optic nerve head), which may be a more accurate indicator of glaucoma susceptibility than IOP alone.

SUMMARY

In a first aspect, the present disclosure provides methods of estimating intracranial pressure in a subject, comprising imaging an intraocular blood vessel while applying a force so as to at least partially applanate (i.e., flatten) or osculate (i.e., curve match), hereinafter referred to as "osculate" or "osculating" unless specifically stated, a portion of the ocular globe so as to increase intraocular pressure to a level sufficient to collapse an intraocular blood vessel; estimating, by one of several methods of determining intraocular pressure, the intraocular pressure that collapses the intraocular blood vessel; and correlating the estimated intraocular pressure that collapses the intraocular blood vessel to an estimated intracranial pressure of the subject. Exemplary methods of determining intraocular pressure include, e.g., corneal applanation tonometry, pneumotonometry, electronic indentation tonometry, transpalpebral tonometry, contour tonometry and the like.

In another aspect, the present disclosure provides systems for measuring intracranial pressure configured to controllably at least partially osculate at least a portion of the ocular globe of a subject's eye, measuring intraocular pressure and suitably collecting images from retinal blood vessels. In one illustrative embodiment, retinal blood vessel images are concurrently collected with a means of determining intraocular pressure from the measured force on the ocular globe and determination of the area of flattening or depression of the ocular globe.

The present disclosure further provides ophthalmic components that may be referred herein as osculating caps. These components suitably include a body having an optical surface adapted to contact a subject's cornea, the body being adapted to engage with an applanating instrument, and the component comprising a lens, a prism, or both. In some embodiments, the lens or prism is formed in the body. In others, the lens or prism is bonded to the body. The osculating cap may contain one or more indicia to assist the ICP measurement system to know its type or function. Further, the indicia may alter or control system electronics to modulate system operation and data collection. The ophthalmic component may, in some embodiments, include a refractive surface approximating that of a unapplanated cornea. The lens, prism, or both, may be formed on one surface of the ophthalmic component.

The present disclosure further provides systems for imaging the retinal fundus concurrently collected with a means of determining intraocular pressure for the purposes of determining intracranial pressure in the presence of papilledema or grading papilledema.

Further yet, the present disclosure provides systems for determining pupillary reflex in response to light stimulation concurrently or sequentially with measuring ICP, IOP or ophthalmodynamometry (ODM).

The present disclosure also provides ophthalmic components, the components suitably comprising a body having an osculating surface adapted to osculate a subject's ocular globe, and the body being adapted to engage with an instrument.

Also provided are methods of estimating a pressure in a subject, the methods suitably comprising imaging an intraocular blood vessel while applying a force to the subject's ocular globe, the force being applied through a component having a contact surface that osculates a portion of the subject's ocular globe, the force being sufficient to collapse an intraocular blood vessel.

Further provided are systems for measuring intracranial pressure in a subject, the systems comprising an ophthalmic component having a having an osculating optical surface adapted to contact a subject's ocular globe; and a force applicator.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale or proportion. In the drawings:

FIG. 8 depicts a second exemplary cross-section view of an illumination pattern of the flat osculation interface in accordance with the present invention.

FIG. 13 depicts methods of increasing pressure in the eye with an osculating cap of the cornea.

DETAILED DESCRIPTION OF ILLUSTRATIVE EMBODIMENTS

Figure 1:
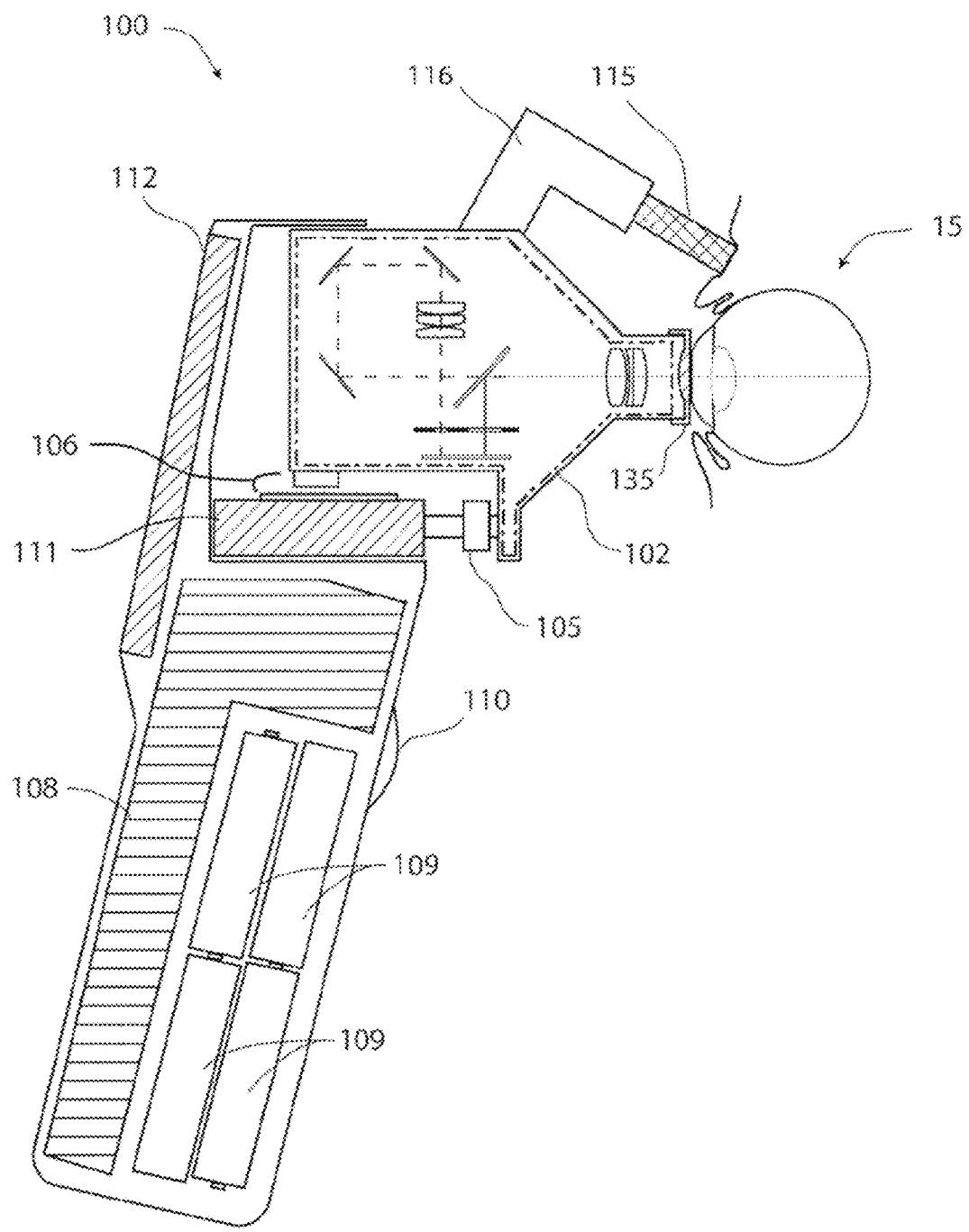
FIG. 1 depicts an exemplary intracranial pressure measuring system according to the present disclosure.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality," as used herein, means more than one. When a range of values is expressed, another embodiment includes from the one particular value and/or to the other particular value. Similarly, when values are expressed as approximations, by use of the antecedent "approximately" or "about," it will be understood that the particular value forms another embodiment. All ranges are inclusive and combinable, and all publications cited herein are incorporated by reference in their entireties for any and all purposes.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges includes each and every value within that range.

To fully describe the application of the disclosed methods and systems to ICP measurement and to describe why pressure in retinal vessels is well-correlated to ICP, a review of the anatomy and physiology of the eye and surrounding tissues is useful. The optic nerve connects the retinal ganglion cell axons within the eye to the brain and is completely surrounded by the subarachnoid space. The subarachnoid space is filled with cerebrospinal fluid (CSF), and the pressure of this fluid is equivalent to ICP. The central retinal artery, vein and central retinal nerve travel through the central region of the optic nerve, converging at the optic nerve head in the back of the eye. As CSF pressure increases, the pressure in the subarachnoid space increases, which exerts an increasing pressure on the optic nerve. This increased fluid pressure in turn applies a pressure around the central retinal vessels that travel within the optic nerve, causing an increase in blood pressure in the central retinal vessels proportional to the CSF constriction pressure.

Changes in ICP are frequently correlated to changes in pupillary reflex. Traditionally, the extent of the pupillary reflex has been subjective and determined by waving a flashlight into a patients eye to observe the pupils reactivity and thus the status of the nervous system and brain [the retinal sensory receptors, sensory fibers (optic nerve II), the brain stem and mid brain, motor fibers (oculomoter nerve III) and the pupillary constrictor muscle in the iris]. In the present invention, changes in constriction and dilatation of pupils in response to light can be quantitatively assessed in the same instrument which has the functionality of an ODM, tonometer, and ICP monitor. Providing the user with these multiple neuro-opthalmic measures and data from pupillometry in a virtually simultaneous or sequential manner will simplify, speed up and significantly enhance the available information to assess the neurological status of the patient. It also offers the ability to use a single device for measuring combinations of ophthalmodynamometry, tonometry, ICP, and pupillometry.

In one aspect, the present disclosure provides methods of estimating intracranial pressure in a subject. These methods include, inter alia, imaging an intraocular blood vessel while applying a force to a subject's ocular globe so as to at least partially osculate at least a portion of the ocular globe and increase intraocular pressure so as to collapse an intraocular blood vessel. The force may be applied directly to the subject's cornea or sclera, but this is not a requirement, as force may be applied to an eyelid (upper or lower) of the subject so as to indirectly applanate a portion of the ocular globe.

The methods also include estimating, suitably by controllably imaging the osculated portion of the subject's ocular globe, the intraocular pressure that collapses the intraocular blood vessel; and correlating the estimated intraocular pressure that collapses the intraocular blood vessel to an estimated intracranial pressure of the subject. This may be performed in an automated fashion, and embodiments where a computer controller and processor act to controllably apply the osculating force and collect images of the osculated portion of the eye and of the blood vessel are considered especially suitable. Embodiments where a computer processor correlates the applanated area of the ocular globe to the applied pressure that collapses the blood vessel are considered suitable.

The at least partially osculated portion of the subject's ocular globe suitably includes a portion of the sclera, a portion of the cornea, or even both. This may be affected by a manually-controlled device or by an automated or computer-controlled device. The user may suitably osculate the ocular globe by pressing directly on the ocular globe. Alternatively, the user may press on an eyelid of the subject so as to osculate the ocular globe. The osculation may be effected by a flat-end rod or other shaped device. Ultrasound probes may be used as osculator, as an ultrasound probe may be used to apply force to the eye, and even to image the blood vessel of the eye, in some cases. In some embodiments, the ultrasound probe may be contacted to the eyelid or the cornea of the subject so as to applanate the ocular globe, with the ultrasound probe also being used to image the blood vessel in the eye.

In some embodiments, the methods suitably include estimating the intraocular pressure that collapses the intraocular blood vessel by correlating one or more images of the osculated portion of the subject's ocular globe to the applied force corresponding to the one or more images of the osculated portion of the subject's ocular globe. The user may image the osculated portion of the subject's ocular globe while applying a first, reference osculation force. Subsequent to or continuous with application of this first reference force, a known increasing force is continuously applied while images of the osculated area are simultaneously obtained.

Concurrent with obtaining images of the osculated area, the user may obtain images of the retina in which the central retinal vessels can be observed. These retinal images may be synchronized with the osculated area images and applied force data so that when a collapse of one of the central retinal vessels is observed in the retinal images, the osculated area and applied force at that moment in time is known.

Knowledge of the osculated area and applied force at that moment allows the user to calculate the intraocular pressure at the time of vessel collapse, and therefore estimate the pressure within the vessel at the time of collapse. Alternatively, osculated area images and applied force data from moments immediately before and/or immediately after the moment of observed retinal vessel collapse may be used to calculate intraocular pressure at the moment of vessel collapse. Other means of measuring intraocular pressure at the moment of collapse can also be utilized in accordance with the invention. For example, osculating the ocular globe and viewing the retinal vessels, synchronized with transpalpebral, pneumatonometric, or contour tonometry estimates of intraocular pressure may be used.

Figure 2:
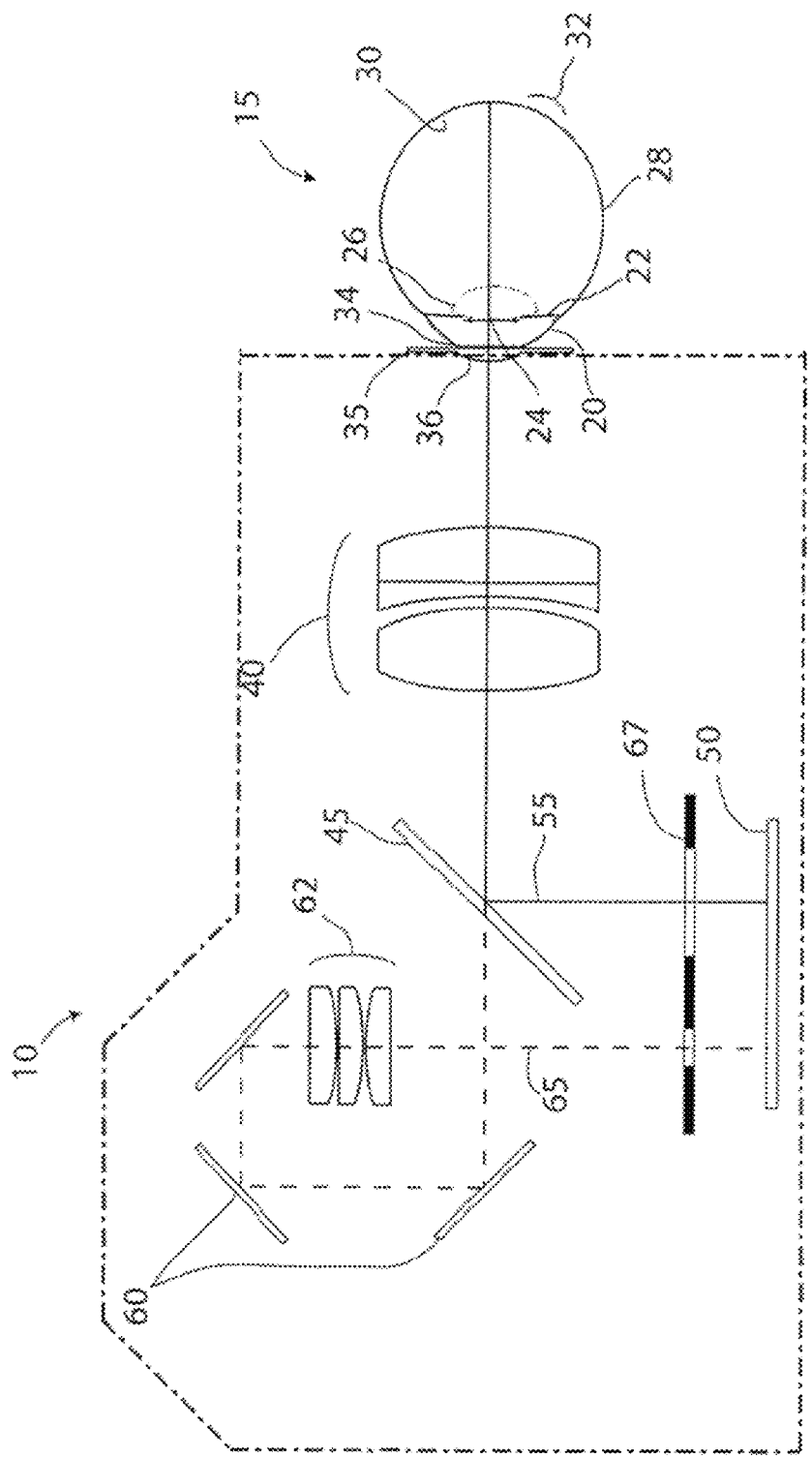
FIG. 2 depicts an exemplary single image sensor optical imaging system according to the present disclosure.

Imaging may, as described herein, be effected by one or more image collectors. As shown in FIG. 2, for example, a user may collect images of the ocular globe and of the collapsed or collapsing blood vessel on a single image detector. Alternatively, a user may employ one image detector to collect an image of the ocular globe and another image collector to collect images of the blood vessel or vessels of interest, as illustrated in FIG. 5.

Figure 5:
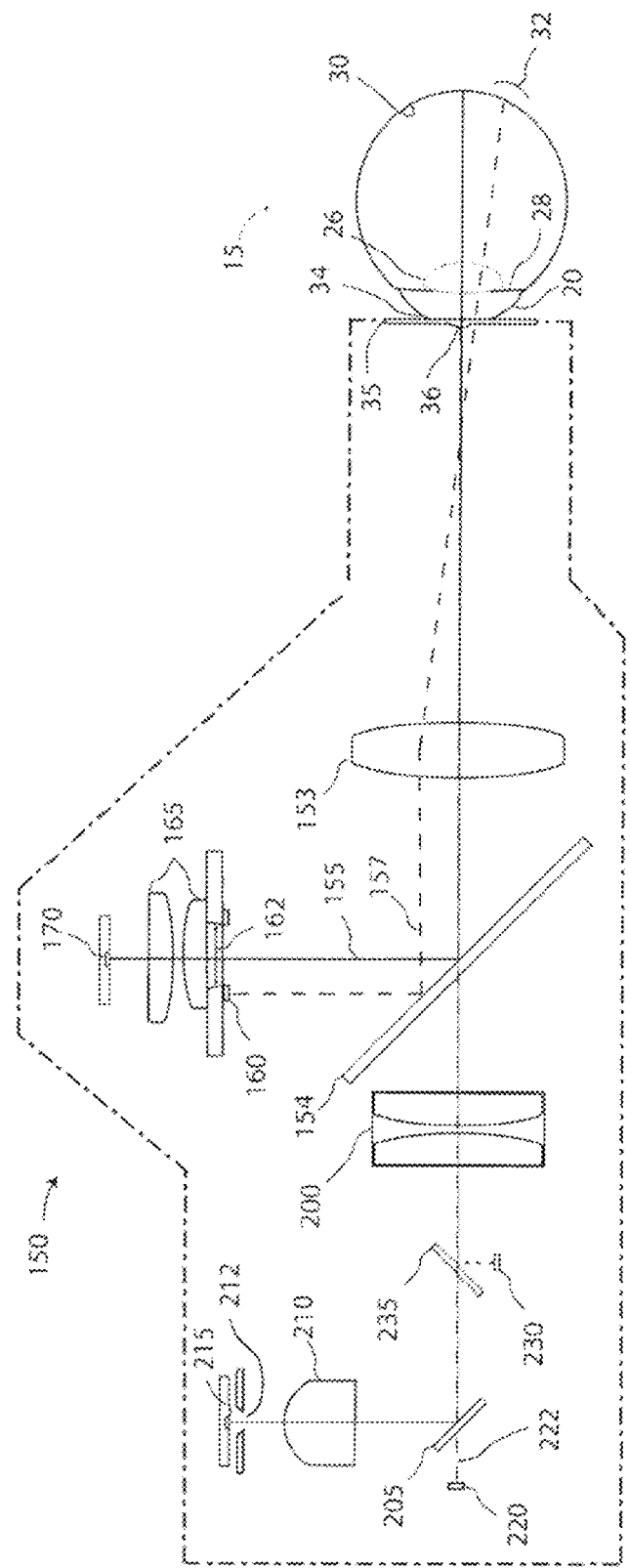
FIG. 5 depicts a first exemplary dual image sensor system according to the present invention.

Osculating the ocular globe to elevate and measure intraocular pressure and to view retinal vessels to determine the point of retinal vessel collapse is one central element that may be accomplished, for example, by sharing optical elements, an imaging axis and imaging sensors as shown in FIGS. 1 and 2 or accomplished using separate optical elements, imaging axes and imaging sensors as shown in FIG. 5 for example. It is understood that imaging of the retina may be accomplished in a variety of optical configurations understood in the art. In the present invention and using such configurations, accommodation may be made to permit concurrent applanation of the ocular globe and determination of intraocular pressure through osculation area and force.

Illustrative FIG. 1 shows an optically clear osculator 135 at the distal end of a device used to applanate the cornea, which also provides an optical pathway through which the retinal images can be obtained. In this embodiment, the central anterior portion of the osculator has a convex-plano (proximal convex shape-distal plano or flat shape) shape to enhance retinal imaging. It should be understood that an osculator may have a plano, convex, concave, a prism, or any combination of surfaces thereof. For example, a osculator may be plano-plano in configuration. Alternatively, an osculator may be a prism-plano. An osculator may also be convex-concave. The convex surface or lens compensates for some or all of the refractive power of the cornea lost when the cornea is flattened or applanated. The osculator may have a plano-plano configuration or may contain other prismatic corrections to image the off-axis optic disk, as convex-plano osculators are not a requirement. The retinal vessels observed in the retinal images may be illuminated by ambient light or by a provided illumination system. The retinal illumination system can comprise an illumination source that is co-axial with the optical path and converge at an apex. Alternatively, in one embodiment the illumination source can comprise multiple off-axis illumination paths.

Estimation of the intraocular pressure at which a central retinal vessel will collapse may be performed by analyzing synchronized retinal images, osculation surface images and force application data. This estimation may be performed during or after the ocular globe has been osculated. In such an estimate the user may review or inspect the retinal blood vessel images, the synchronized osculation surface images and the force applied to the ocular globe to determine the intraocular pressure at the moment of collapse of the intraocular blood vessel. A function can be derived based on using the resting IOP as an initial condition and the calculating the amount of fluid displaced from the anterior chamber as the cornea is applanated. For example, for an eye with a resting IOP of 10 mmHg (millimeters mercury), a 9.8 gram-force to applanate an area of 38 square millimeters would result in an IOP estimate of 18 mmHg. With a resting IOP of 15 mmHg, a 12 gram-force to applanate an area of 34 square millimeters would result in an IOP estimate of 25 mmHg. One exemplary method of estimating IOP (e.g., for applanated areas greater than 3.06 mm in diameter) is set forth by Eisenlohr et al., *Brit J. Ophthal.* (1962) 46, 536).

In some embodiments of the present invention, the methods include automated or semi-automated determination of the pressure that collapses the intraocular blood vessel. In such embodiments, the user may employ an automated image processing algorithm that compares sequential images of the intraocular blood vessels to determine the moment in time when collapse of the central retinal blood vessel occurs, and therefore through the synchronized data the osculating force at that moment in time. One or more of the optical density, color, and caliber of the vessels will change upon vessel collapse, and these characteristics are suitable for automated or manual determination.

Imaging the intraocular blood vessel is suitably accomplished by collecting an image of the retinal fundus on an image collector. Suitable image collectors include focal plane arrays, such as CCD devices, CMOS devices, and the like. The focal plane array may be a two-dimensional array such as those available from Aptina (San Jose, Calif.), or Cypress Semiconductor Corporation (San Jose, Calif.), or even be a linear array such as those available from Goodrich Corporation (Princeton, N.J.).

The periocular arteries that supply blood to tissues and structures of the eye pass through the cerebral spinal fluid (CSF) and are sensitive to changes in CSF pressure. Systolic and diastolic blood flow velocities are subject to a complex auto-regulatory process in which the periocular arteries continue to supply sufficient blood circulation to the eye even when a patient has an elevated ICP. As pressure increases surrounding the blood circulation to the eye, various blood flow parameters in the central retinal and ophthalmic arteries are also affected.

The user may, in some embodiments, obtain Doppler ultrasound information from a periocular blood vessel of the subject to improve the accuracy of correlation between the present invention and invasive measurements of ICP. Periocular blood vessels within the cranium are located within or close to the eye. Examples include the ophthalmic artery, the central retinal artery and vein, superior and inferior ophthalmic veins, the middle cerebral artery, etc. Locating a periocular blood vessel is suitably performed by insonating the vessels that supply the ocular globe and exit the cranium through the optic canal or cavernous sinus. Auditory and/or visual signals without imaging may also be used to indicate that a vessel has been identified. An example of an auditory signal may include changes in sound pitch in response to changes in blood flow. An example of a non-imaging visual signal may include a linear LED array that lights successive LED's in response to increased sensed blood flow.

A variety of blood flow parameters may be used in estimating ICP (see, e.g., U.S. Pat. No. 7,122,007 to Querfurth, incorporated herein by reference in its entirety). Pulsatility index ("PI"), resistivity index ("RI"), systolic velocity, diastolic velocity, and the like are all suitable velocity indicia for use in the system. PI is considered a particularly suitable velocity parameter for use in the system. Blood velocity in vessels within the cranium is affected by intracranial pressure. Blood velocity, particularly in the arteries, is not constant for a given intracranial pressure, but varies in relation to the status of the cardiac cycle. Maximum blood velocity is termed "peak systolic blood velocity", and corresponds to maximum heart contraction. Minimum blood velocity occurs during the time that the heart is filling with blood (diastole) and is termed "end diastolic blood velocity."

$$PI = \frac{\text{(Peak systolic velocity} - \text{End diastolic velocity)}}{\text{Mean velocity}}$$

$$RI = \frac{\text{(Peak systolic velocity} - \text{End diastolic velocity)}}{\text{Peak systolic velocity}}$$

As pressure increases surrounding the blood circulation to the eye, the resistivity and pulsatility of the blood flow in the central retinal and ophthalmic arteries are also affected.

It has been determined that intracranial pressure can be accurately estimated as a function of ophthalmic parameters including central retinal venous pressure (CRVP) and arterial blood velocity (ABV), where ABV may be assessed using PI, RI, or another blood velocity metric:

$$ICP = f(CRVP, ABV)$$

Using sequential measurements from multiple devices one may fit data to the form ICP=A+Bx. Following the methods and systems described herein, one such functional relationship may be expressed in the form ICP=A+Bx+Cy, where x is central retinal vein pressure (CRVP) and y is the pulsatility index (PI) of the ophthalmic artery. A, B and C are scalars used to fit clinical data and depend on the manner of which the ophthalmic parameters are collected. For instance, A and B can be adjusted based on the method of tonometry (e.g., pneumotonometry, transpalpebral, contour tonometry or applanation) and C can be adjusted based on the periocular vessel chosen for the measurement. By way of example and based on clinical experience following the methods and systems described, one may correlate the CRVP plus the Doppler ultrasound pulsatility index of the ophthalmic artery to ICP using the following regression equation:

$$ICP = 0.294 + 0.735(CRVP) + 0.735\left(\frac{1}{PI}\right).$$

ICP functions like the one above may be further improved in accuracy by including additional independent variables. The embodiments described herein focus on ophthalmic parameters not previously considered in a unified expression; biomechanical variables including but not limited to optic disc swelling or other ocular biomechanical properties that are affected by elevated ICP. These peripapillary ophthalmic parameters can be incorporated into an independent ophthalmic tissue variable (OT), in units of stress. Thus:

$$ICP=f(CRVP, ABV, OT).$$

In addition, patients in need of a determination of intracranial pressure may, in some cases, also have papilledema, a swelling of the optic disc that occurs secondary to elevated intracranial pressure. Papilledema develops in a stepwise fashion, and can be tracked by medical professionals using a widely accepted grading scheme first proposed by Frisén (Stavern 2007 "Optic Disc Edema" in Seminars in Neurology, vol. 27, no. 3, pages 233-243, 2007); and S. Echegaray, "Automated Analysis of Optic Nerve Images for Detection and Staging of Papilledema" (in Investigative Ophthalmology and Visual Science, vol. 52, no. 10, pages 7470-7478, 2011). The Modified Frisén Scale classifies papilledema into six grades from 0 (normal) to 5 (severe). Each grade is characterized by a set of objective, visual features observed on the optic disc and peripapillary retina. A device that captures images of the optic disc and surrounding peripapillary retina and classifies papilledema using the Frisén grading method will not only provide the ability to objectively assess papilledema severity, but will be able to use the level of papilledema severity as an input to an algorithm for more accurately determining ICP. Various implications and assessment of ICP are discussed in U.S. patent application Ser. No. 12/959,821 (filed Dec. 3, 2010), the entirety of which is incorporated herein by reference for all purposes.

Another method of assessing papilledema severity in order to more accurately determine ICP is to use ocular coherence tomography (OCT) to measure peripapillary retinal nerve fiber layer (RNFL) thickness. Swelling of the peripapillary retina due to elevation in ICP will cause an increase in the RNFL thickness. Therefore, a technique that can provide RNFL thickness can be used to improve an algorithm for determining ICP.

For example, one such variable, the severity of papilledema present in some patients with elevated ICP, may be used to modify the above equation. Papilledema and its associated swelling of the tissues of the optic disc and surrounding retina due to an increase in axoplasmic fluid surrounding the axons, may cause an increase in bulk tissue pressure ($P_{BT}$). This bulk tissue pressure will contribute (along with the cerebrospinal fluid pressure, or ICP) to the overall pressure being applied to the central retinal vein. The magnitude of $P_{BT}$ is correlated with the severity of papilledema, and may therefore correlate with the papilledema grade from the modified Frisén scale (MFS). In this case OT is a function of $P_{BT}$ or, OT=f($P_{BT}$). One may use MFS to obtain OT or, OT=f(MFS).

Another method of assessing papilledema (and therefore assessing $P_{BT}$) is to use OCT to measure peripapillary RNFL thickness. OCT is a non-invasive technique that provides cross-sectional images of the RNFL and provides absolute measurements of the fiber layer thickness. Increases in the thickness of this fiber layer are directly correlated to the severity of papilledema, and so OT=f(RNFL). Incorporating the OT component into the ICP functional equation above yields:

$$ICP = A + B(CRVP) + C\left(\frac{1}{PI}\right) - D(OT),$$

where A is directly proportional to the Frisén Scale papilledema grade. As set forth above, a user may estimate intracranial pressure by basing that estimate at least in part on an assessment of the degree, of any, of papilledema that may be present in the subject. The papilledema assessment is suitably based on the Frisén or modified Frisén scale. The assessment may be performed in an automated fashion. One such approach to an automated assessment of papilledema presence is set forth by S. Echegarry et al. Alternatively, the assessment of papilledema may be made by way of optical coherent tomography (OCT), as described herein.

Accordingly, as set forth above, the present disclosure provides methods of assessing the intracranial pressure of a subject. These methods include, inter alia, estimating intracranial pressure by combining an assessment of the level of papilledema, if any, present in the subject with one or more of a blood velocity of the subject, a blood vessel pressure of the subject, a tissue thickness of the subject, or any combination thereof. The tissue thickness may, for example, be the thickness of the retinal nerve fiber layer, the thickness of the prelaminar optic nerve head tissue, or some combination of these. The blood velocity may be a systolic velocity, a diastolic velocity, or any combination thereof, such as the PI and RI indices described herein. The papilledema level comprises a Frisén scale score of the papilledema. The assessment of the papilledema level, the tissue thickness, or both, is based on optical coherent tomography (OCT) or other methods to measure peripapillary RNFL thickness, prelaminar optic nerve head tissue thickness, or other ocular tissues.

The present disclosure also provides systems for measuring intracranial pressure in a subject. These systems suitably include a portion (the "osculating cap") to controllably at least partially osculate (i.e., at least partially flatten or curve match) at least a portion of the ocular globe of a subject's eye. This osculation may be effected by contacting the eye with an osculation surface or even by an ophthalmic component, which may also be referred to as the osculator. It should be understood that the osculation may be effected by applying a force to, e.g., the eyelid of the subject, the cornea or sclera of the subject, or two or more of the foregoing.

The systems suitably include at least a first image collector configured to collect light from an intraocular blood vessel of the subject's eye, and a retinal illumination train that may be configured to direct light through an ophthalmic component (which may be referred to as an osculating cap) to the intraocular blood vessel of the subject's eye and to direct light reflected from the intraocular blood vessel to the image collector and a microprocessor. An image collector may be configured to view the intraocular blood vessel in the absence of a system illumination train. For example, a sensitive, low-light image sensor may be used to collect images illuminated by ambient light. Alternatively, an infrared sensitive image sensor may also be used. The osculating cap (as one illustrative ophthalmic component) may be sterile and removably affixed or otherwise engage with an optical module (which may be referred to collectively as the optical train). The optical module and motion of the osculator may be a motor-controlled as describe below, but may also be manually controlled and advanced.

The system of the present disclosure can be configured using one or more focal plane array image sensors for imaging the retina and the osculated portion of the ocular globe of the subject. In one embodiment a single image sensor is configured to collect images from both the retina and the interface between the cornea and an osculation area (which may be referred to as "corneal imaging" or "corneal image"). The images can be collected simultaneously or in rapid and repeating succession. A single image sensor system may be configured into a light weight, compact system. In a single sensor system the image sensor may be required to continuously collect high-speed images for applanation analysis and high-resolution images of retinal vessel analysis. Alternatively, rapid sequential image collection may be utilized that require the single sensor to sequentially change from high-speed low-resolution to low-speed high-resolution data collection. Presently, sensors operating in either configuration are suitable but relatively expensive.

In another embodiment, two separate arrays may be utilized for retinal and corneal image capture to overcome the limitations of a single sensor system. A system has been effectively constructed using a first sensor to collect images from the retina and a second sensor to collect images from the osculated portion of the ocular globe.

The motion of the optical train may be manually-controlled. Alternatively, the optical train may be computer-controlled. Any suitable method of advancing the osculator onto the surface of the ocular globe can be used. Electromagnetically driven mechanisms, e.g. a voice coil motor, were successfully clinically tested. However, other motion control mechanisms such as conventional and stepper motors, pneumatic actuators and the like may also be utilized. Electromagnetically driven mechanisms, including voice coil motors, have added advantages. In addition to inducing controllable displacement of the osculator, they also produce an electrical indication of the force being exerted. Further, inflatable accordion-style osculating caps may be used.

The osculator may be of any material compatible with the cornea such as polycarbonate, polymethyl methacrylate (PMMA), polyethylene (e.g., LDPE) or even glass. Transparent materials are especially suitable for the osculator and ophthalmic components. The osculator diameter can range from about under 4 mm to over 15 mm. One parameter that may at least partially determine the osculator size is the degree to which the ocular globe is osculated. For an adult cornea, a convenient size is 10 mm. The osculator may suitably be transparent, although transparency is not a requirement. The osculator may be translucent or opaque as well, which may be suitable for use when the applanation portion (e.g., ophthalmic component or osculting cap) contacts the eyelid or sclera. In some embodiments, the osculator includes a lens, prism, or both formed in a plano body.

The osculating cap may have an engagement portion configured to engage with an optical module suitably movable for contact with the ocular globe. The osculating cap is suitably constructed to be sterile and removably affixed to the optical module and able to snap on, screw onto, be magnetically held or otherwise affixed thereto. The cap may be reusable or disposable.

The osculating cap may bear one or more indicia. These indicia (which may be present in the form of letters, numbers, barcodes, or even electronic form) may be used to identify the applanation cap in terms of clinical use, size, shape, or other characteristic. For example, a particular index may convey that the osculating cap bearing the index is sized for use in pediatric patients. Since a child's ocular globe is smaller than an adult's, use of an appropriate osculating cap may eliminate the need for focus adjustments and associated mechanical and optical complexity. Further, it can notify system electronics of the requisite operating parameters (maximum force, etc.) that can be exerted on the child's eye.

The disclosed methods and systems may be used for indications other than traumatic head injury. For example, when measuring resting intraocular pressure in patients with glaucoma or ocular hypertension, one would not require an osculating cap incorporating retinal imaging compensation optics. The indicia will notify the system parameters of the device's intended use and settings and, in this case, appropriately limit the osculation force. In this manner, a system may include a set of one or more osculating caps so as to accommodate subjects that are themselves different. For example, an emergency medical team might maintain a set or kit of multiple caps so as to accommodate patients of various sizes. The systems and methods may also be configured obtain a translaminar pressure (i.e., the pressure difference between IOP and ICP that is applied to the optic nerve head), which may be used as a more accurate indicator of glaucoma susceptibility than IOP alone. Further yet, the system can be configured for measuring pupillary reflex.

In some embodiments, the ophthalmic component is configured so as to direct light reflected from the intraocular blood vessel to the first image collector. The ophthalmic component may also be configured to direct an image of the osculation interface between the ophthalmic component and an osculated region of the ocular globe to the first image collector. The system may be configured to direct an image of the collapsing or collapsed blood vessel and an image of the osculation interface to a single image collector, as illustrated in FIG. 2. In other embodiments, the images are directed to separate image collectors, as illustrated in FIG. 5

In some embodiments, the system is capable of self-configuring in response to indicia on the osculating cap. For example, the system may adjust the osculator, the image collector, or even the illumination train in response to one or more indicia present on the cap. As one example, an auto-focus motor could pre-adjust the location of the imaging sensor prior to the beginning of data collection, corresponding to the patient's eye size (as indicated by the choice of osculating cap).

The system may be configured such that during operation it concurrently applies a force to the subject's ocular globe and collects, from an image collector, images from at least one of an intraocular blood vessel of a subject's eye and an interface between the osculation area and the ocular globe of the subject's eye. Applanation of the cornea and simultaneous visualization of the retina has been found to be a particularly convenient configuration. In this configuration, osculation does not cause lateral movement of the ocular globe or distort the view of retinal vessels. In addition, all measurements are made along the same axis. In certain embodiments, the system is configured to, during operation, concurrently osculating at least a portion of the subject's ocular globe and collect, on the first image collector, light reflected from the intraocular blood vessel of the subject's eye.

An illumination train may, in some embodiments, include one or more light sources such as a light-emitting diode (LED), an incandescent lamp, an electroluminescent light source, and the like. In some embodiments and as most clearly shown in FIG. 6 in conjunction with FIGS. 7 and 8, the illumination train includes light-emitting diodes arranged in a circular or ring configuration. It should be understood that light emitted from the light sources may have a wavelength in the visible light range (wavelength approximately 400 nm to 700 nm), but may also be infrared light (wavelength approximately 700 nm to over 1,200 nm). Thus, the term "light" as used herein shall be understood to mean energy in the visible and near infrared regions of the electromagnetic spectrum.

Systems may also include a fixation illuminator configured so as to provide a reference point for the subject to align the ocular globe. Such illuminators may be a light source upon which the subject focuses while the system is operating on the subject. In this way, the subject's eye is stabilized and maintains a consistent orientation during operation of the device.

Systems may further include a Doppler instrument configured so as to collect ultrasound data from a periocular blood vessel of the subject. Examples of periocular blood vessels include the ophthalmic artery, the central retinal artery and vein, the lacrimal artery, posterior ciliary arteries, superior and inferior ophthalmic veins, and middle cerebral artery. Ophthalmic artery insonation requires penetration of approximately 40 to 50 mm. For this amount of tissue penetration, an ultrasound probe of between 7 MHz and 10 MHz is preferred. Locating a periocular blood vessel is suitably performed by using a color Doppler ultrasound imaging system. Examples of such devices are commercially available from General Electric (www.ge.com) and Philips (www.philips.com). Alternatively, a non-imaging Doppler ultrasound system with auditory and/or visual feedback signals locate a periocular blood vessel by scanning the anatomical volume of interest using a linear probe can be used. One such device is an ultrasound transducer manufactured by Multigon Industries. The Doppler sensor may be adjustably fixed to the body of the invention as shown in FIG. 1 or may be separately held.

The systems may, in some embodiments, be configured so as to be capable of assessing the degree, if any, of papilledema present in the subject. In one illustrative embodiment, the system is configured to obtain one or more images of the fundus of the subject and compare at least one of these images to a library image of a fundus, and generate a papilledema grade for the subject. The system may include a processor configured to estimate intracranial pressure of the subject based on one or more images of the at least partially osculated area of the subject's eye and one or more images of the intraocular blood vessel of the subject's eye. The papilledema assessment method of S. Echegaray et al., is considered especially suitable for application to the disclosed systems and methods.

The systems in the present disclosure may include an osculating cap configured to controllably contact an applanation portion (which may also be referred to as an ophthalmic component, an osculator or osculation area) to the ocular globe of a subject's eye. Suitable osculators and osculating caps are described elsewhere herein. The systems may also include an image collector configured to collect light reflected from an intraocular blood vessel of the subject's eye. The system may also include an illumination train configured to direct light through the osculator to the intraocular blood vessel of the subject's eye and to direct light reflected from the intraocular blood vessel to the image collector. During operation, the system may record retinal fundus images and score features of the optic disc using image processing algorithms known to those of skill in the art. The system may be configured to compare feature scores to a database of images for the purpose of grading papilledema according the Modified Frisén scale. The system may be configured to output a Frisén scale score of papilledema paired with an image of the optic disc for purposes of tracking papilledema progression. The system may thus assess a subject's papilledema and assess the patient's condition over time. In some configurations, the system generates a papilledema score in an automated fashion. The systems may be configured to, during operation, record retinal fundus images, score features of the optic disc using image processing algorithms, or both. The systems may also be configured to compare feature scores to a database of images for so as to grade the purpose of grading papilledma, if present, according the Modified Frisén Scale.

Further disclosure is now made by reference to the attached figures.

FIG. 1 illustrates a cutaway view of an exemplary intracranial pressure measuring system according to the present disclosure. As shown, ICP measuring system 100 suitably includes a movable optical module 102 that engages with the osculator 135. In this embodiment, Osculator 135 has a flat applanation surface. A motion control module 104 (not shown) may modulate the motion of the optical module 102 and the osculator 135. Electronics module 108 contains units adapted to control and modulate the device's actions and operations. Optical module 102 collects retinal images simultaneously with electronic module 108 collecting force and position data from force transducer 105 and position sensor 106, respectively. Motion of optical module 102 to applanate a portion of ocular globe 15 may be manual or automatic. Automatic motion of the optical module is suitably controlled by motor 111, force transducer 105 and position sensor 106. Optical module 102 suitably translates in a range of several centimeters, e.g., by 0.5, 1, 2, 3, 4, or even 5. During operation and upon contact with the cornea, force transducer 105 limits the force to appropriately safe levels of intraocular pressure and the portion of ocular globe 15 osculated. Position sensor 106 may limit translation to under approximately 4 mm (subject to the size of the subject's eye) so as not to harm the subject. Following data collection, which nominally takes approximately 5 to 10 seconds, optical module 102 automatically retracts. If desired by the user, a scroll wheel, lever, slide or the like may be used to review the osculation force and the images of the retina on display 112 collected during actuation so as to identify the instant of vessel collapse. The identification of the instant of vessel collapse may also be automatic.

Figure 12A:
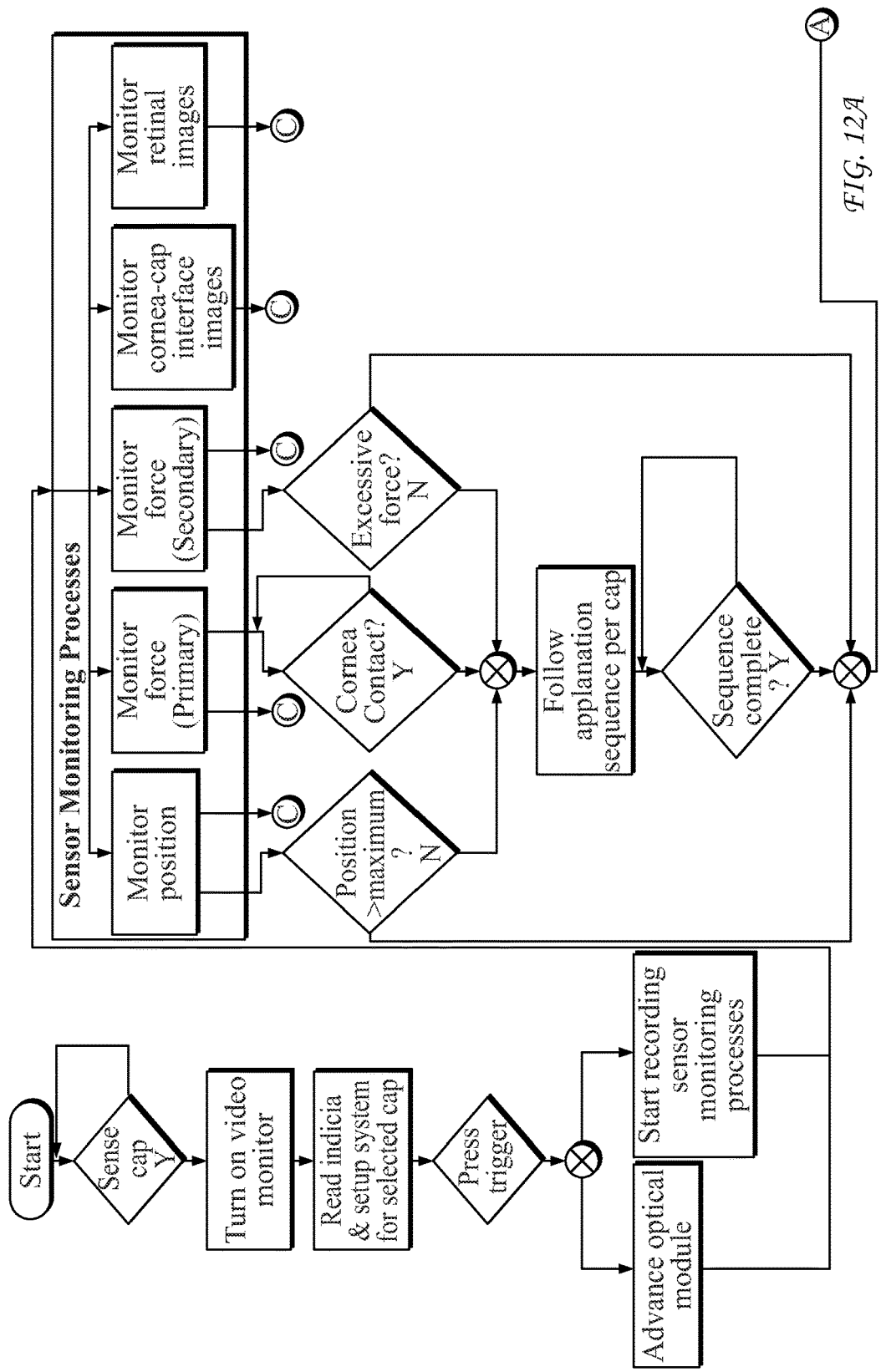
FIG. 12 depicts an exemplary flow diagram of the operation of an intracranial pressure measuring system.
Figure 12B:
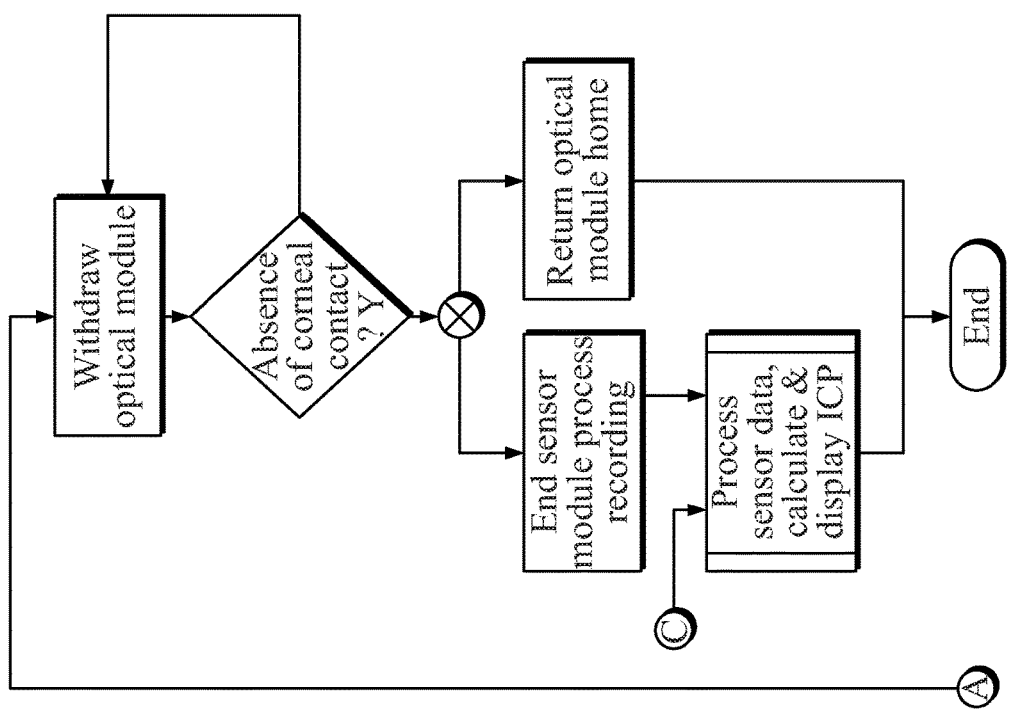

The sensor used to determine force applied to the ocular globe may be any form of force transducer, including one or more of electrical resistance, foil, semiconductor or thin film strain gauges and other force measurement devices. Force transducer 105 can be located in any position in ICP measuring system 100 that will provide a signal proportional to the force applied to the ocular globe. As shown, force transducer 105 is positioned between motor 111 and the movable optical module 102. The determination of force by sensing a change in the current from a voice coil motor 111 drive is of particular value due to use of a single device to drive the optical module and sensitively measure the forces exerted. Locating a force transducer in close proximity to osculator 135 may be advantageous. Position sensor 106 provides information on the absolute position and velocity of the osculating cap. Several position sensors are readily available for this application. Hall effect sensors have been found to be suitably small, inexpensive and accurate. However, other sensors including but not limited to inductive sensors, linear variable differential transformer (LVDT) sensors, etc. may be used. ICP measurement system 100 may be equipped with a head support (not shown) so as to stabilize the position of the device on the subject. For the convenience of the operator and safety of the subject, optical module 102 and osculator 135 may be positioned such that osculator 135 will not touch the subject's ocular globe until the system is stabilized on the subject and determined appropriate by the operator. Batteries 109 may be used to power the device. The device may also run off of household or commercial electrical lines. A trigger 110 may be used to actuate the device, e.g., to advance the osculator, or take one or more images, or to effect one or more other action FIG. 12 depicts an exemplary flow diagram of the operation of an intracranial pressure measuring system. Upon powering on the apparatus ("Start"), the system senses the presence of an osculating cap and turns on the video monitor. System electronics setup the system per information provided in the selected cap's indicia. After placement of the system over the subject's eye (not shown in flow diagram), the operator depresses a trigger 110 to simultaneously advance the optical module and initiate recording of data from the five sensors. A position sensor is monitored to determine the optical modules location and velocity. A primary force sensor senses the force required to advance the cap and optical module as detect the increase in force resulting from contact with the ocular globe. A secondary force sensor is monitored to insure that the force measured by the primary force sensor is within safe limits; else the optical module is withdrawn. A sequence of movements of the optical module is followed in accordance with the cap indicia information. Once the sequence is completed, the optical module is withdrawn from the cornea, sensor monitoring processes cease, data is analyzed and the value of ICP is displayed.

The embodiment shown in FIG. 1 also illustrates Doppler ultrasound transducer 115 suitably mounted on transducer pivot arm 116 to permit contact of Doppler transducer 115 in the periocular region and oriented towards the ophthalmic artery. A signal such as an auditory signal varies in pitch and volume that may help the operator aim the probe in the correct orientation. The Doppler device may be constantly collecting Doppler ultrasound data using either an auditory or visual feedback signal. Once transducer 115 is correctly positioned, pulsatility data may be collected and averaged over at least three heart cycles.

FIG. 2 depicts an exemplary optical configuration of a single image sensor system 10 according to the present disclosure. In such an ICP measurement system, a first image may be collected of optic disc region 32 of retina 30 and focused on a first portion of retina/cornea image sensor 50 so as to distinguish a collapsed blood vessel such as the central retinal vein. A second image may be collected indicative of the degree of applanation of the ocular globe and focused on a second portion of retina/cornea image sensor 50. Exemplary retinal imaging path 55 is also shown, as is corneal imaging path 65.

A portion of ocular globe 15 is flattened by osculator 35. In the embodiment shown, the portion of ocular globe 15 that is osculated is cornea 20. The distal surface of osculator 35 is shown as a flat or plano surface and proximal side is shown as a convex surface (referred to as "osculator lens 36"). Light reflected from retina 30 passes through ocular lens 26, flattened cornea 20, osculator 35 and objective lens 40. Objective lens 40 may be comprised of one or more lenses. The light reflected from retina 30 is then reflected by dichroic beam splitter 45 onto retina/cornea image sensor 50. Light from retina 30 may be reflected from an external source of illumination (not shown). In one exemplary embodiment, retina 30 is illuminated using visible light source at 565 nm. Any number of dichroic beam splitter 45 could be utilized such as, for example purposes only, a 580 nm single-edge long-pass dichroic beam splitter that reflects >95% of wavelengths in the range of 350 nm to 570 nm and transmits 93% of wavelengths from 591 nm to >950 nm (Semrock, Inc., Rochester, N.Y.). Alternatively, light from retina 30 may be infrared energy emitted as a result of heat from retina.

Osculation of cornea 20 by osculator 35 causes flattening of the cornea and a resulting change in the pattern and intensity of light reflected by the cornea onto retina/cornea sensor 50. The force required to flatten cornea 20 increases with increased osculation. It is well known that by measuring the force required to osculate (applanate) the cornea to a known area (typically 3.06 mm in diameter) one may estimate the resting intraocular pressure. So-called corneal applanation tonometry has been one standard means of measuring intraocular pressure for screening and routine management of patients with ocular hypertension and glaucoma.

In traditional applanation tonometry, corneal flattening substantially under 3.06 mm results in loss of measurement accuracy due to effects of corneal rigidity and tear-film complications. Flat osculation (applanation) of the cornea to an area substantially greater than 3.06 mm decreases the accuracy of the measurement to greater than accepted norms of +/−0.5 mmHg. This is due to an induced increase in the patient's intraocular pressure. As a result, applanating the cornea beyond 3.06 mm is generally contraindicated, although the 3.06 mm applanation area is not a requirement or limit. In the present invention, the operator suitably elevates intraocular pressure so as to intentionally generate intraocular pressure sufficient to collapse the retinal vasculature. Estimating IOP for osculation areas greater than 3.06 mm requires modeling of the biomechanics of the cornea to determine pressure as a function of force and area. A function can be derived based on using the resting TOP as an initial condition and the calculating the amount of fluid displaced from the anterior chamber as the cornea is osculated. One exemplary method of estimating TOP (e.g., for applanated areas greater than 3.06 mm in diameter is set forth by Eisenlohr et al., *Brit J. Ophthal.* (1962) 46, 536).

Flattened cornea 20 can be visualized and the area of osculation determined by imaging cornea-osculator interface 34 using an image sensor illuminated by any wavelength sensitive to the image sensor. However, it is preferable to select a wavelength different from that used to illuminate retina 30. In the example above using the described beam splitter and retina illumination (not shown), cornea illumination source (not shown) was selected to be an 850 nm LED. It is preferable, but not a requirement, that the retina be illuminated by 540 nm to 570 nm green light. Such wavelengths provide excellent contrast and enhance visibility of the retinal vasculature. Light reflected by flattened cornea 20 passes through osculator 35, objective lens 40 and dichroic beam splitter 45. Bending mirrors 60 positions reflected cornea light to pass through corneal imaging lens assembly 62 and corneal portion (left) of aperture 67 and focus the corneal image on retina/cornea image sensor 50. Aperture 67 serves to reduce unwanted vignetting and backscatter of illumination from the system optics and anatomical structures such as the lens and cornea.

Figure 3:
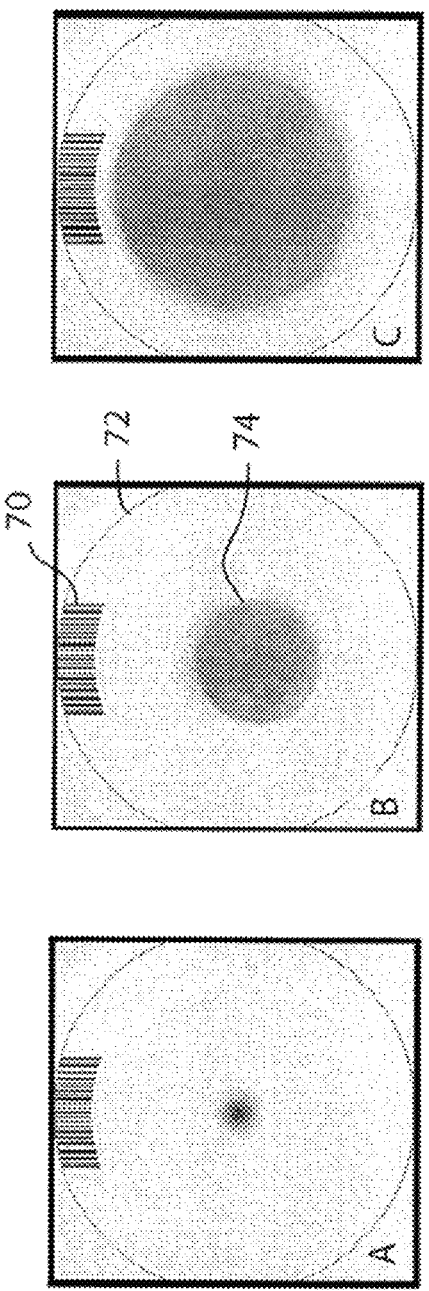
FIG. 3 depicts exemplary results of imaging a flat osculator according to the present invention.

FIG. 3 shows the results of illuminating osculation interface 34 of a porcine cornea using near infrared light. However, similar results are obtained using visible illumination light. A portion of the illumination light reaching osculator interface 34 will be reflected back and be visible by retina-cornea image sensor 50. Indicia 70 are also shown. The reflection is the result of the differences in the index of refraction between the osculator and either ambient air or aqueous from the subject's tear film. When the osculator is in contact with the cornea, the contacted portion of the illumination light is transmitted through the osculator and will appear darker when viewed by the image sensor as shown as applanation area 74. Thus, the darker circle will grow in size as greater force is exerted on the cornea. In this example, the pressure in the pig's eye was initially set at 10 mmHg with a manometer. Incremental increases in force on the ocular globe will result in incremental increases in intraocular pressure above the initially set 10 mmHg. Maximum osculation area 72 is shown as a circular line as a reference to the user. In this example and upon contact of the osculator with the pig's eye, the results are as follows:

|  | Diameter/Area | Force | Measured pressure |
| --- | --- | --- | --- |
| FIG. 3A | 0.91 mm/0.007 cm$^2$ | 0.50 gF | — |
| FIG. 3B | 3.54 mm/0.098 cm$^2$ | 1.06 gF | 10.8 mmHg |
| FIG. 3C | 6.31 mm/0.313 cm$^2$ | 3.55 gF | 11.3 mmHg |

Figure 4:
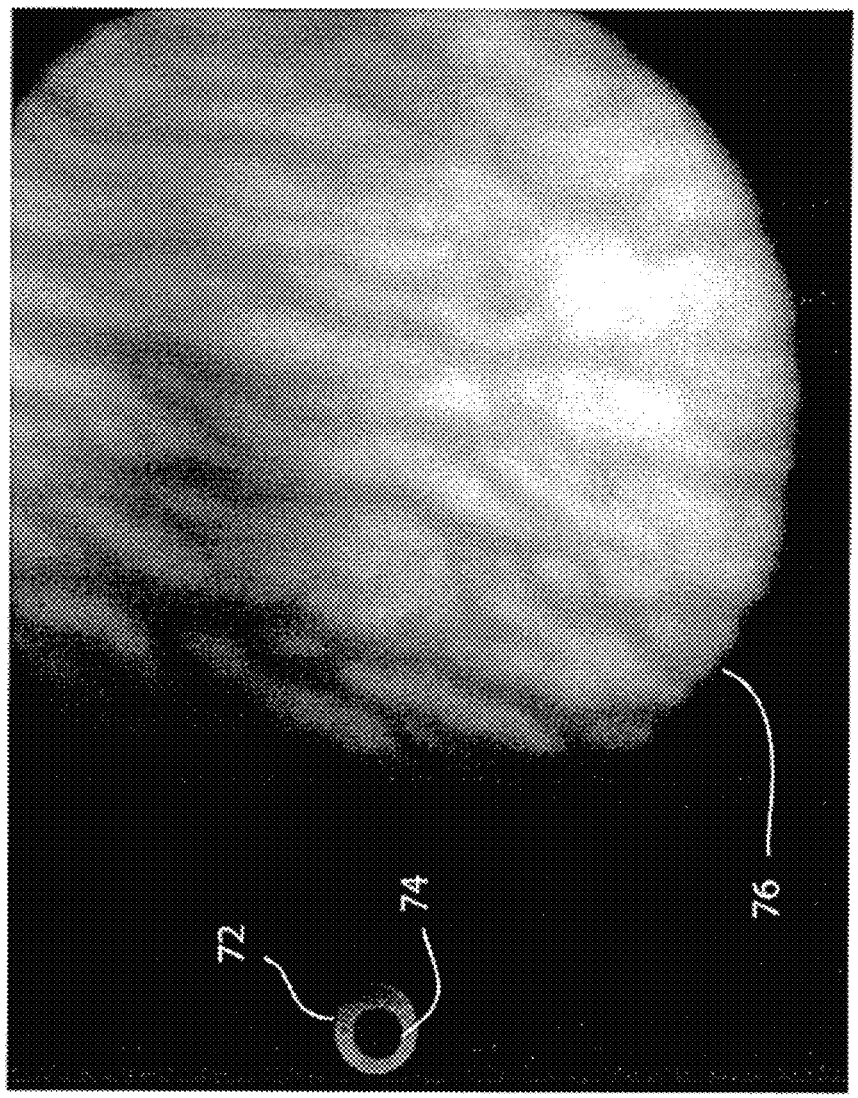
FIG. 4 depicts an image from a single retina-cornea image sensor system according to the present disclosure.

FIG. 4 shows an image taken by a single retina-cornea image sensor system similar to that shown in FIG. 2. The larger retinal fundus 76 and smaller corneal applanation area 74 were taken of a rabbit. In the image shown, a 1.3 megapixel (1280 H×1024V) CMOS sensor was used. However, the selection of sensor depends upon the design of the optical train, the illumination, the desired field of view, the frame rate, etc. A person of skill in the art will select appropriate optical and opto-mechanial elements to meet the desired system specifications. A large field of view and high-resolution image is beneficial for retinal imaging. The large retinal field of view allows for more rapid identification of the optic disk. Higher resolution also permits the ability to electronically select the area of interest and maintain sufficient resolution to observe vessel collapse. In this illustrative example, satisfactory retinal images were obtained using approximately 1024×1024 px field. In contrast, determination of corneal osculation area was effectively obtained using a 256×256 px field.

FIG. 5 depicts an exemplary dual sensor system 150 according to the present invention. This system provides retinal illumination and imaging, corneal illumination and imaging, and a fixation point as described below.

Figure 6:
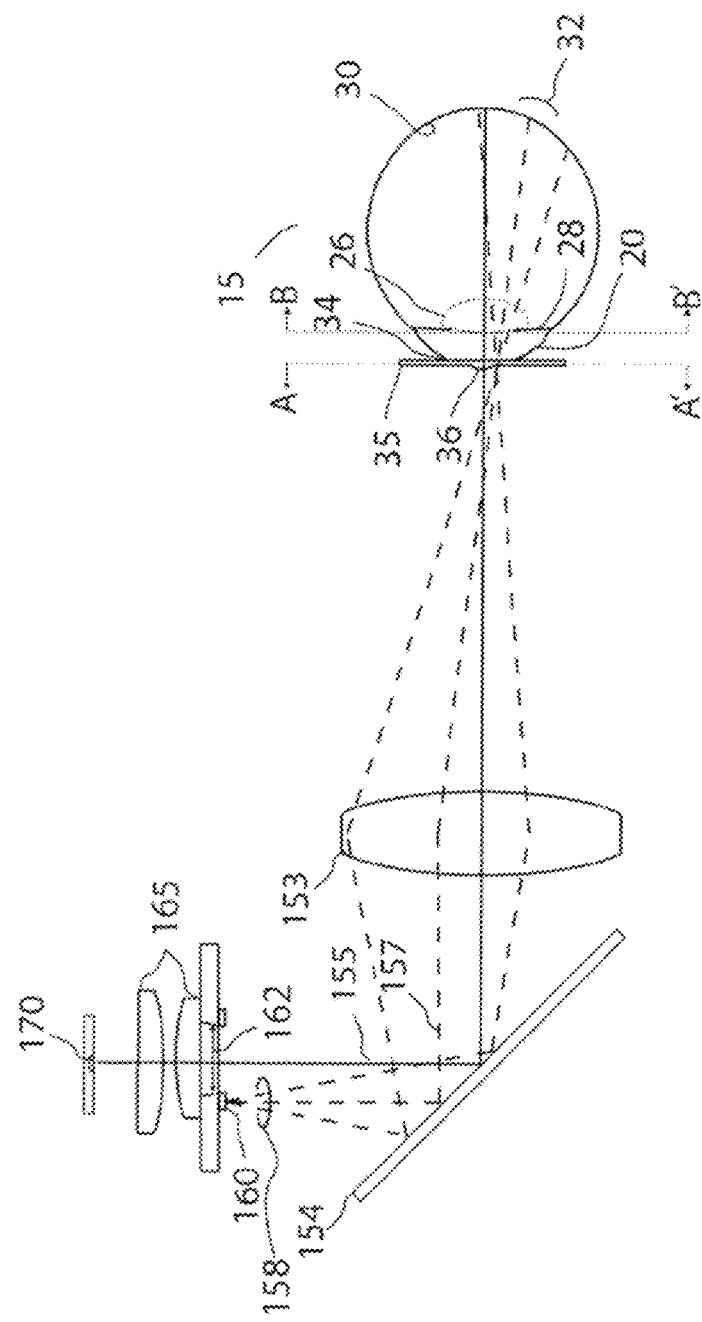
FIG. 6 depicts an exemplary retinal imaging and illumination system shown in FIG. 5 and according to the present invention.

For convenience, the retinal illumination aspect of the system 150 is described first and is highlighted in FIG. 6. While reference to retinal illumination is used herein, it should be understood that reference to the 'retina' or 'retinal' is to include blood vessels leading to and from the retina and more particularly the central retinal artery and vein.

Figure 7:
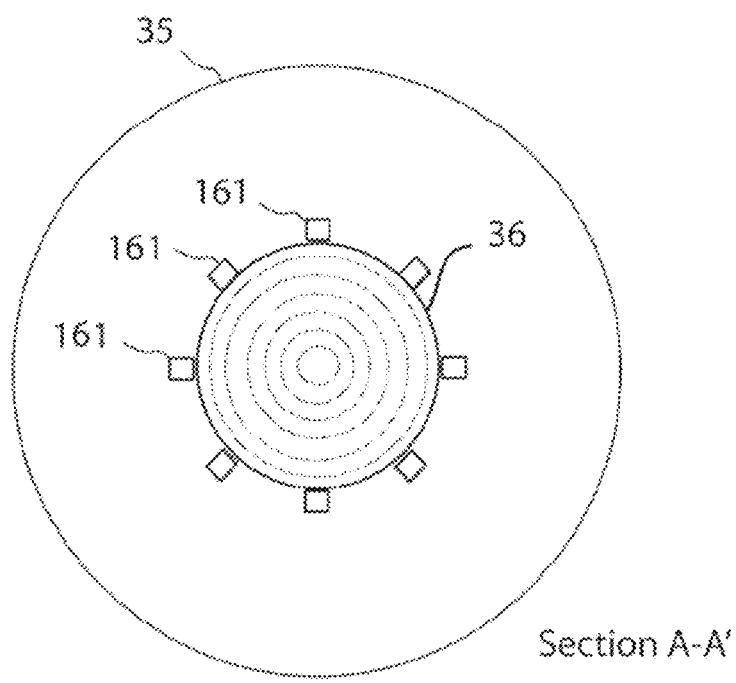
FIG. 7 depicts a first exemplary cross-section view of an illumination pattern of the flat osculation interface in accordance with the present invention.

Retinal illumination light source 160 may be a ring of light sources including for example light emitting diodes (LED's) that emit light along path 157 (one LED illustrated for simplicity of the explanation and shown as a dotted line). Retinal illumination light 158 is reflected by dichroic beam splitter 154, passes through and is focused by objective lens 153 and is incident on osculator 35. As shown in FIG. 6 and in cross-section A-A' in FIG. 7, retinal illumination light 158 is focused and forms a circular illumination pattern 161 on osculator 35 peripheral to convex shaped cap lens 36. Cap lens 36 serves to compensate for the refractive power of the cornea lost due to osculating (flattening) cornea 20. Retinal illumination light 158 diverges and forms illumination pattern 161 as it passes through pupil formed by iris 28. Section B-B' in FIG. 6 shown in cross section in FIG. 8, illustrates the relative size of retinal illumination pattern 161 in the plane of iris 22. A constricted iris may vignette a portion of the light, yet provide sufficient illumination to image retina 30 on retina image sensor 170 through an un-dilated, 2.4 mm pupil. However, adequate illumination through smaller diameter pupils is also possible. In this embodiment and as shown in FIGS. 6, 7 and 8, illuminating the retina through illumination path 157 peripheral to cap lens 36 and central pupil 24, obviates the illumination path being coaxial with retina imaging path 155 that is positioned along the central optical axis of ocular globe 15. The sclera is shown but not labeled. However, in this configuration, both illumination and imaging paths share objective lens 153. As a result this configuration minimizes or eliminates illumination light reflected back to retina image sensor 170 from objective lens 153, osculator 35, cornea 20 and ocular lens 26. Various image stops or apertures such as retinal image aperture 162 may be added to further reduce stray light from entering retina image sensor 170. One or more focusing lenses 165 may be present to adjust retinal or other lighting. Corneal focusing lens 210 may also be present.

Figure 11:
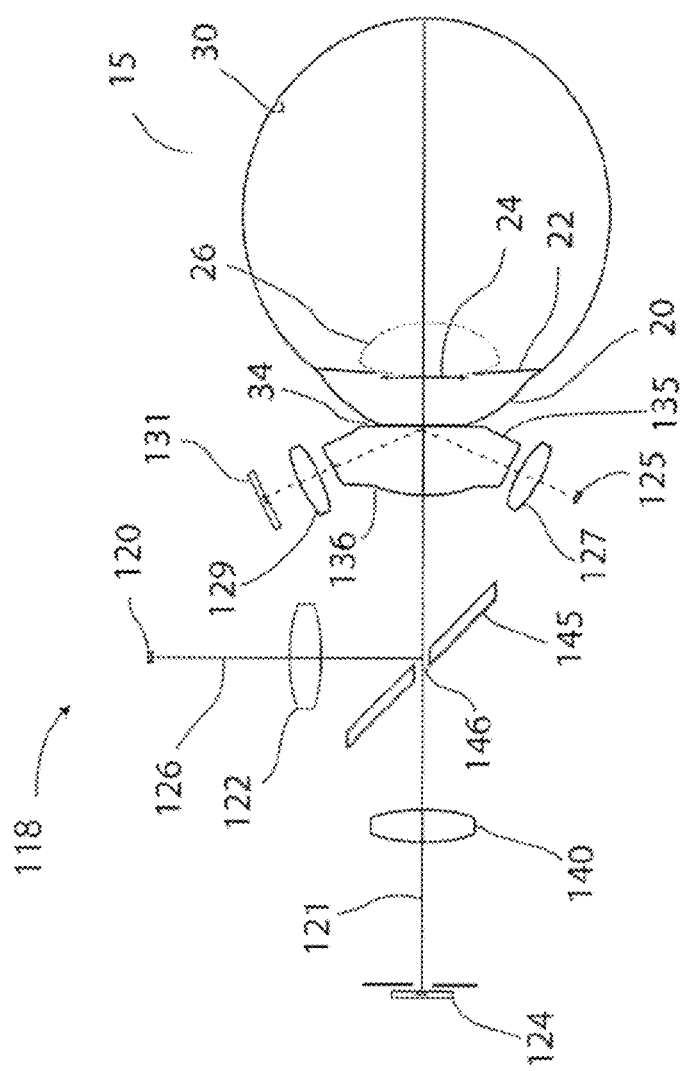
FIG. 11 depicts a second exemplary dual image sensor system according to the present invention.

There are numerous techniques known in the art to illuminate the retina with light entering the eye through the central pupil. For example a total reflecting mirror with an aperture positioned along the illumination axis may be used in place of dichroic beam splitter 154. This is shown in FIG. 11 as aperture 146 in aperture mirror 145. In this configuration a ring of illumination light is created thereby minimizing reflections back to the retinal image sensor.

Figure 9A:
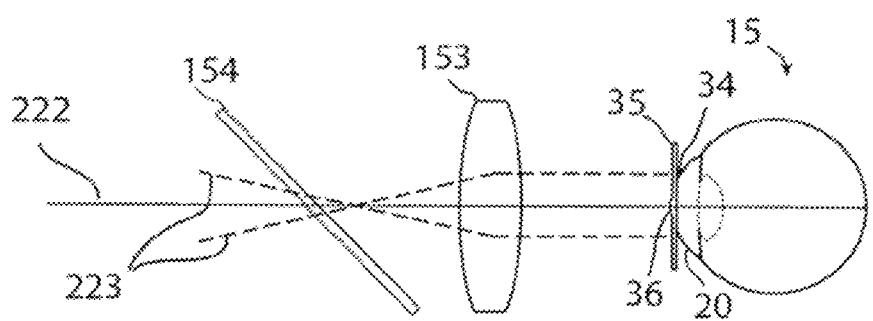
FIG. 9A depicts a portion of a corneal imaging and illumination system shown in FIG. 5 and according to the present invention.

FIG. 5 shows a scheme for illuminating and imaging osculation interface 34 along the central axis of the ocular globe and sharing objective lens 153. Cornea illumination source 220 light passes through dichroic beam splitters 205 and 235. Field lens 200 focuses illumination source light to an apex in proximity to dichroic beam splitter 154. Illumination light is then collimated by objective lens 153 onto osculator 35 as better shown in FIG. 9A illustrating cornea illumination rays 223. The collimated illumination light is reflected by osculator 35 back to dichroic beam splitter 205 and corneal focusing lens 210, aperture 212 onto corneal image sensor 215. Retinal image axis 155 is shown. Cornea illumination path 222 is shown, as well. Fixation light source 230 is also shown.

As used in one illustrative corneal applanation imaging system, osculator 35 is flat plane of PMMA with a very small, 2 mm in diameter lens 36. The incident illumination light will be normal to flat plane of osculator 35. Therefore, the reflectance, R, from each surface, proximal and distal, with a refractive index $n_0$ of air=1 and a refractive index $n_1$ of PMMA=1.492, is given by $$R_P = \left[\frac{(n_0 - n_1)}{(n_0 + n_1)}\right]^2.$$

Therefore, 3.9% of the incident light is reflected from the proximal surface of the cap and 3.9% from the distal surface where the cap is not osculating the cornea. When the distal surface of osculator 35 is contacting cornea 20 having an index of refraction $n_C$=1.33, the distal surface will reflect $$R_D = \left[\frac{(n_1 - n_C)}{(n_1 + n_C)}\right]^2 = 0.3\%.$$

Figure 9B:
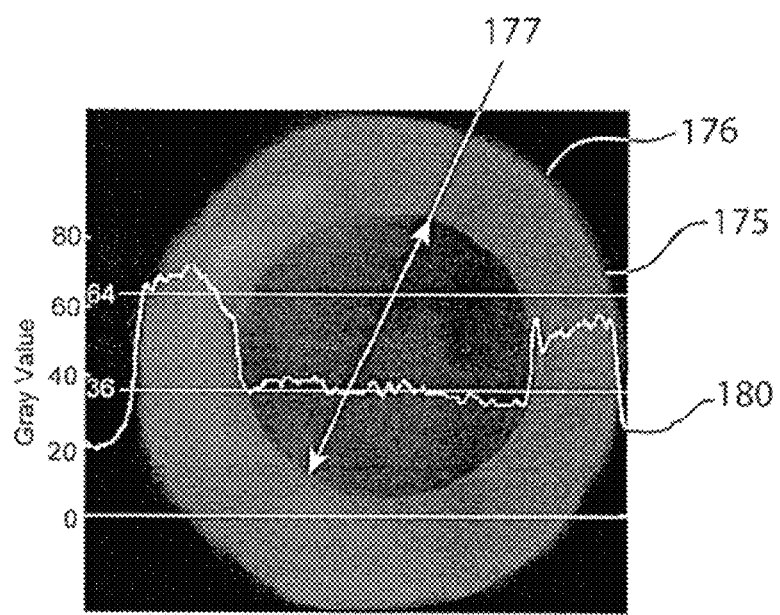
FIG. 9B depicts a corneal osculating image from the system shown in FIG. 5 and according to the present invention.

As a result, the osculated surface of osculator 35 cornea will reflect 3.9%+0.3% or 4.2% of the incident light and the non-applanated area will reflect 3.9%+3.9% or 7.8%. Thus cornea image sensor 215 will show an almost 2:1 contrast ratio of osculated to non-osculated areas on contact. FIG. 9B illustrates an osculated area using collimated light. In this example, darker osculated area 177 has a grey value of approximately 36 and is surrounded by lighter maximum osculation area 176 having a grey value of approximately 64. 175 represents an applanation image.

Figure 10:
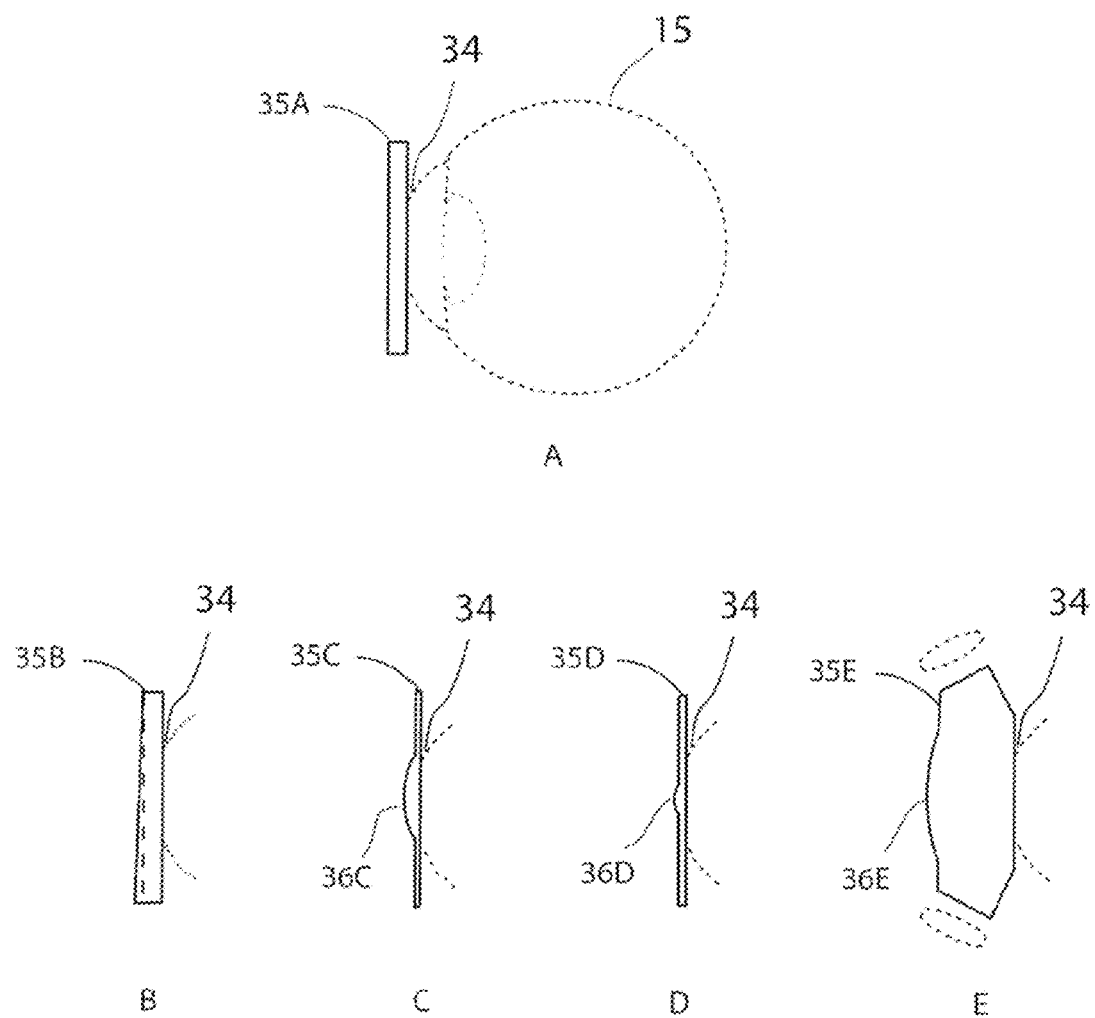
FIG. 10 depicts exemplary flat osculators in accordance with the present invention.

FIG. 10 depicts various plano distal end configurations of the osculator that are within the scope of the present disclosure. Alterations in the proximal refractive surface of an osculator provide a host of optical design options. For example, FIG. 10A shows the cornea of ocular globe 15 being applanated by plano-piano osculator 35A. As shown, the function of the cap is solely to applanate the cornea. Upon applanation, the pressure in the eye will be elevated and there will be complete loss of the refractive power by the cornea. Conventional fundus cameras are dependent on corneal refractive power to view the retina. As a result plano-piano osculator 35A eliminates use of such camera to view the retina. Further, such cameras have no means to simultaneously view the cornea.

The configuration of the system shown in FIG. 5 and highlighted in FIGS. 6 and 9A overcome the limitations of a conventional fundus camera while providing a path for simultaneous imaging of the cornea 20. Such a configuration will permit viewing the retina along the optical axis of the eye centered on the fovea. The optic disc, from which the optic nerve and central retinal artery and vein enter the retina, is located approximately 3 mm nasal and 1 mm superior to the fovea.

FIG. 10B illustrates osculator 35B, which is similar to flat Osculation cap 35A but has a prismatic element permitting a shift in the image of the retina. This may permit viewing the retina with the system aligned along the optical axis of the eye, but centered on the optic disc. FIGS. 10C, D and E show osculators 35C, 35D and 35E with lenses 36C, 36D and 36E respectively. These lenses have suitably positive (convex) surfaces on the proximal surface to replace some or all of the optical power of the cornea lost during applanation. The configuration and size of the osculation cap and osculator lens is chosen in concert with the rest of the optical module. Three representative optical module configurations are illustrated herein and are not to be viewed as limiting. Other optical module configurations and osculator can be designed within the teaching and spirit of the invention by one of skill in the art.

As stated, the osculator may be of any material compatible with the cornea such as polycarbonate, polymethyl methacrylate (PMMA) or even glass. The osculator diameter can range from about under 4 mm to over 15 mm.

The parameter that determines the osculator diameter is the degree of ocular globe osculation. For osculating an adult cornea, a convenient size is 10mm. This diameter does not include the area for handling or conveniently mounting the osculator to the osculating cap.

In another embodiment of the disclosed invention, a conventional optical configuration for viewing the retinal fundus is used that does not share the optical path for viewing osculation area of the ocular globe. While corneal osculation techniques for collapsing the retinal vessels and determination of intraocular pressure is one preferred embodiment, it is understood that osculation may be accomplished by osculating of the sclera as well. However, any means of osculation can be used that can be configured to permit a view of the blood vessels within the optic disk and determine intraocular pressure. Suitable methods may include but not be limited to corneal applanation tonometry, pneumotonometry (also referred to a 'air-puff tonometry"), electronic indentation tonometry, transpalpebral (through the eyelid) tonometry, and the like.

FIG. 11 depicts an exemplary embodiment based on use of a retinal fundus viewing system that does not share an optical path with the path used for measuring osculation area. Several retinal imaging and illumination configurations are well known in the art, one of which is shown in this embodiment. Osculator 135 is positioned to osculate the cornea and form osculation interface 34. Osculation interface 34 is preferably flat but may be shaped to accommodate placement on the cornea and modifications in the intraocular pressure measuring scheme. As shown in this figure, retinal illumination source 120 emits light along retina illumination path 126, which light is directed by lens or lenses 122 and is reflected by apertured mirror 145. Apertured mirror 145 has aperture 146 positioned along retinal imaging path 121. Aperture 146 permits an un-obscured optical path for imaging the retina. Further, it does not reflect retinal illumination along the central axis of imaging path 121, and as a result it reduces or eliminates light reflected back toward retinal imaging sensor 124. Retinal illumination is transmitted through and focused by osculator lens 136, passes through pupil 24 and suitably reflects from one or more intraocular blood vessels of retina 30. Osculator lens 136 is a convex surface on proximal side of osculator 135 designed to replace some or all of the refractive power of the cornea during applanation.

Light reflected from retina 30 passes through pupil 24 and osculator 135 and is focused by osculator lens 136 to an apex at or near aperture 146. Reflected light is then focused by retinal focusing lens or lenses 140 onto retina image sensor 124.

An exemplary cornea osculation area measurement scheme is also shown in FIG. 11. Corneal illumination source 125 projects illumination light by way of corneal illumination lens 127 to osculation interface 34. As described herein and as a result of changes in the index of refraction at the cornea and osculating cap interface, the pattern of light at osculation interface 34 changes as a function of the force applied and resulting degree of applanation of the cornea by osculator 135. The pattern of reflection and resulting intensity of illumination light from the osculation interface 34 is focused by cornea imaging lens 129 onto cornea image sensor 131. Thus, ICP measuring system 118 is suitable to simultaneously image the degree of osculation by osculator 135 on the cornea and, image blood vessels in the optic disc of the retina. Imaging axis 121 is also shown. An imaging aperture (not labeled) may be present in communication with the image sensor 124.

The disclosed systems are not limited to the imaging or illumination arrangements shown in the figures. In one of several variations, light from the illumination source 120 may be one or more LED's configured to pass through an axicon lens (not shown) forming a ring of light directed by a dichroic beam splitter to osculator 135.

The conventional lenses in the ICP measurement system have been discussed herein. However, such lenses can be replaced using similarly functioning optical elements including diffractive lenses, holographic optical elements, graded index lenses and hybrid optical elements.

The present disclosure provides additional methods and related systems and devices for increasing pressure in the eye. These will now be described in additional detail.

In one aspect, the present disclosure provides ophthalmic components. These components suitably include a body having an osculating surface adapted to osculate a subject's optical globe, with the body being adapted to engage with an instrument.

It should be understood that the component may osculate with a subject's eyelid, cornea, or sclera. Corneal osculation is considered especially favorable, but is not required.

The osculating surface may be flat, as shown in FIG. 13A. Alternatively, the osculating surface may be characterized as being a concave optical surface that has a radius of curvature, as shown in FIG. 13B. The radius of curvature may, in some embodiments, be greater than the radius of curvature of a subject's ocular globe, e.g., the subject's cornea. Such a radius of curvature may be greater than about 7 mm or even greater than about 8 mm. The surface need not necessarily have a constant curvature; i.e., the surface may include a flat portion and a curved portion, or have a curvature that varies in some fashion across the surface. The osculating surface may be a rigid material, such as PMMA or other polymers.

Alternatively, the osculating surface maybe flexible or even deformable, as shown in FIG. 13D. The component may be configured such that it defines an enclosed control volume in mechanical communication with the osculating surface, as shown in FIG. 13C and FIG. 13D. The control volume is, as shown in FIG. 13D (and as described elsewhere herein), configured to be pressurized while in contact with a subject's ocular globe. In one approach, a component having such a control volume is maintained against the ocular globe (e.g., cornea) of the subject, and the control volume is then pressurized, the pressure in turn exerting a pressure against the cornea, which pressure may be increased so as to collapse an intraocular blood vessel (e.g., a retinal vein). The user may then use that collapsive pressure as an estimate (or in arriving at an estimate) of the intracranial pressure of the subject. Further description of this application is provided elsewhere herein.

As shown in FIG. 13C and FIG. 13D, the disclosed components may include a passage or passages that place the control volume into fluid communication with the environment exterior to the control volume. This passage may be an aperture formed in the component. The passage may also comprise a tap, tube, or other protrusion from the component. A pressurizing unit (e.g., a syringe pump or other fluid source) may then connect to the component so as to provide pressure to the control volume.

Although not shown in the appended figures, a component may also include a force applicator (e.g., a magnetic drive, a servo, and the like) that is incorporated into the component. In these embodiments, the user may connect the component to an instrument that controllably actuates the force applicator of the component. In other embodiments, the component engages with a device that in turn advances the component against the subject as illustrated in FIG. 1 or, alternatively, pressurizes a control volume within the component.

The component may define a control volume of from about 0.01 ml to about 100 ml; control volumes in the range of from 1 ml to about 10 ml are considered especially suitable.

An osculating surface of the disclosed components may suitably comprise a material having a thickness in the range of from about 0.005 inches to about 0.060 inches, although these ranges are not exclusive or otherwise limiting.

A variety of materials may be used in the disclosed components. An osculating surface may suitably include a material having an ultimate elongation of from about 200% to about 1000%, a 300% modulus of from about 1.5 MPa to about 4.0 MPa, an ultimate tensile strength of from about 20 MPa to about 40 MPa, or a combination of these.

Figure 15:
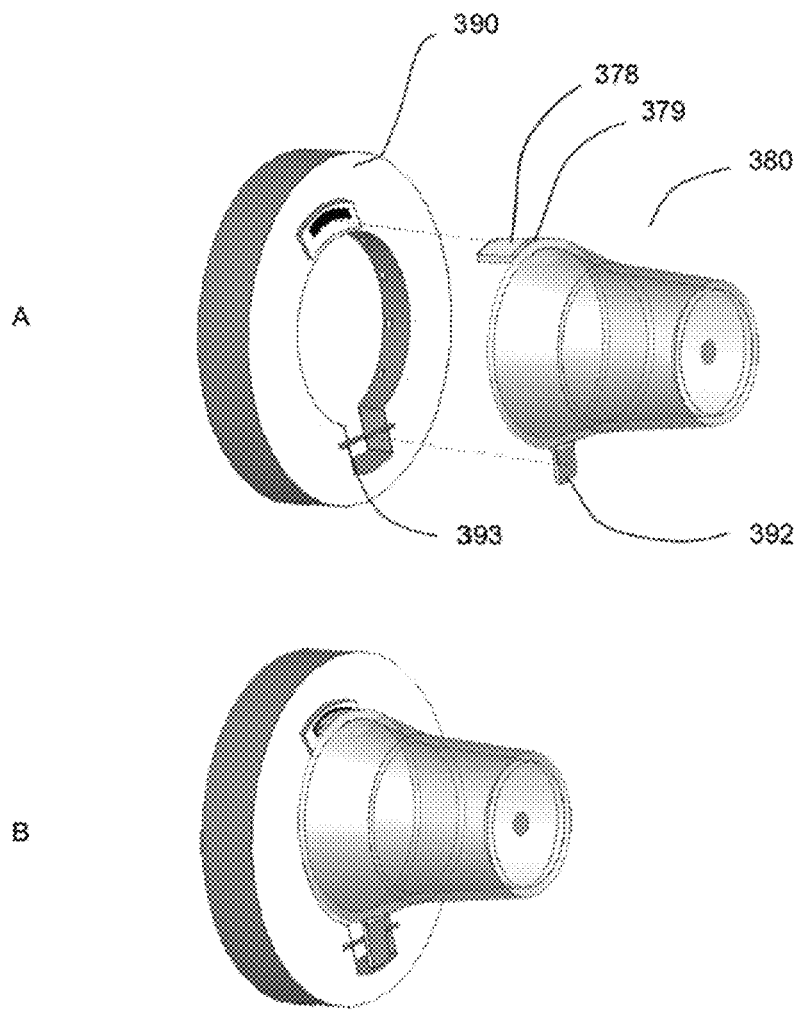
FIG. 15 depicts an exemplary osculating cap mounted on the distal end of an optical train for determining contact force using a deflecting tab.

Components according to the present disclosure may also include a projection (which may also be termed a "tab"), such as tab 378 in FIG. 15A. Such a projection may be adapted to engage with an engagement region (e.g., a tab-slot engagement) of an instrument or other component. One exemplary embodiment is shown in FIG. 15, which is described in additional detail elsewhere herein.

A component may also include a deflectable projection. The deflectable projection suitably comprises a material (e.g., a mirrored material) that is reflective to electromagnetic radiation. As described elsewhere herein, deflection of the projection may be monitored so as to determine a pressure exerted on the component.

Components may also include (not shown) a lens. The lens may be configured so that it is in optical communication with the osculating surface. A lens may also be configured to permit a user to observe or even illuminate the pupil of the subject or even an intraocular blood vessel within the subject's eye.

Figure 17:
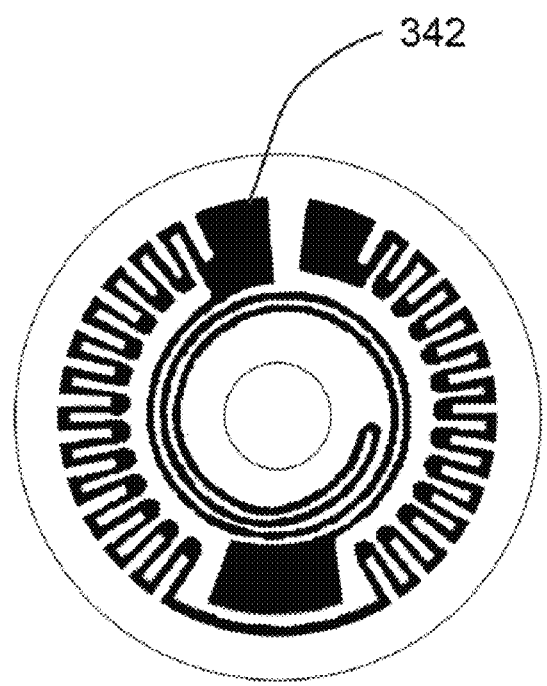
FIG. 17 depicts an exemplary strain gauge pattern for measuring contact forces exerted on an osculator

A component may also be constructed such that the component comprises a strain gauge. One such embodiment is shown in FIG. 17, which is described in more detail elsewhere herein. In such an embodiment, deflection caused by applanation/osculation causes an elongation of the material of the strain gauge and a related measurable change in electrical resistance. As shown in the figure, the strain gauge may comprise a strain gauge pattern disposed on the component, the strain gauge pattern being configured to measure deflection of a portion of the component during contact with a subject.

The present disclosure also provides methods of estimating a pressure (e.g., an intraocular pressure, intracranial pressure) in a subject. These methods suitably include imaging an intraocular blood vessel while applying a force to the subject's ocular globe, the force being applied through a component having a contact surface that osculates a portion of the subject's ocular globe, and the force being sufficient to collapse an intraocular blood vessel.

It should be understood that the term "imaging" does not require a photographic or videographic image. Imaging should be understood to encompass, e.g., the use of ultrasound to obtain an image of a region (e.g., blood vessel) of interest. Imaging also encompasses MRI, CT, and other techniques that permit visualization of a region of interest without also requiring illumination of that region. In one exemplary embodiment, a user may image an intraocular blood vessel within the eye by ultrasound while applying a force to a subject's ocular globe while the subject's eyelid is closed. In this way, a user may assess the condition of a subject that is sleeping or even unconscious.

A user may also correlate a force that collapses the intraocular blood vessel to an estimated intracranial pressure of the subject. Various methods for doing so are described elsewhere herein and in U.S. patent application Ser. No. 13/309,920, the entirety of which is incorporated herein by reference.

The force may be applied to, e.g., the cornea of the subject, to the sclera of the subject, to the eyelid of the subject, or a combination thereof. It should be understood that force may be applied at a discrete location, across an area, or even at two or more separate locations of a subject's ocular globe.

Force may be applied in a variety of ways. In one embodiment, force may be applied by physically advancing the component against the subject. This may be accomplished by using a screw drive, a magnetic drive, a servo, or other device to advance the component against the subject. In some embodiments, at least some of the force may be applied by increasing a pressure within the component so as to exert a force against the subject, as shown in FIG. 13D and associated description.

Figure 16:
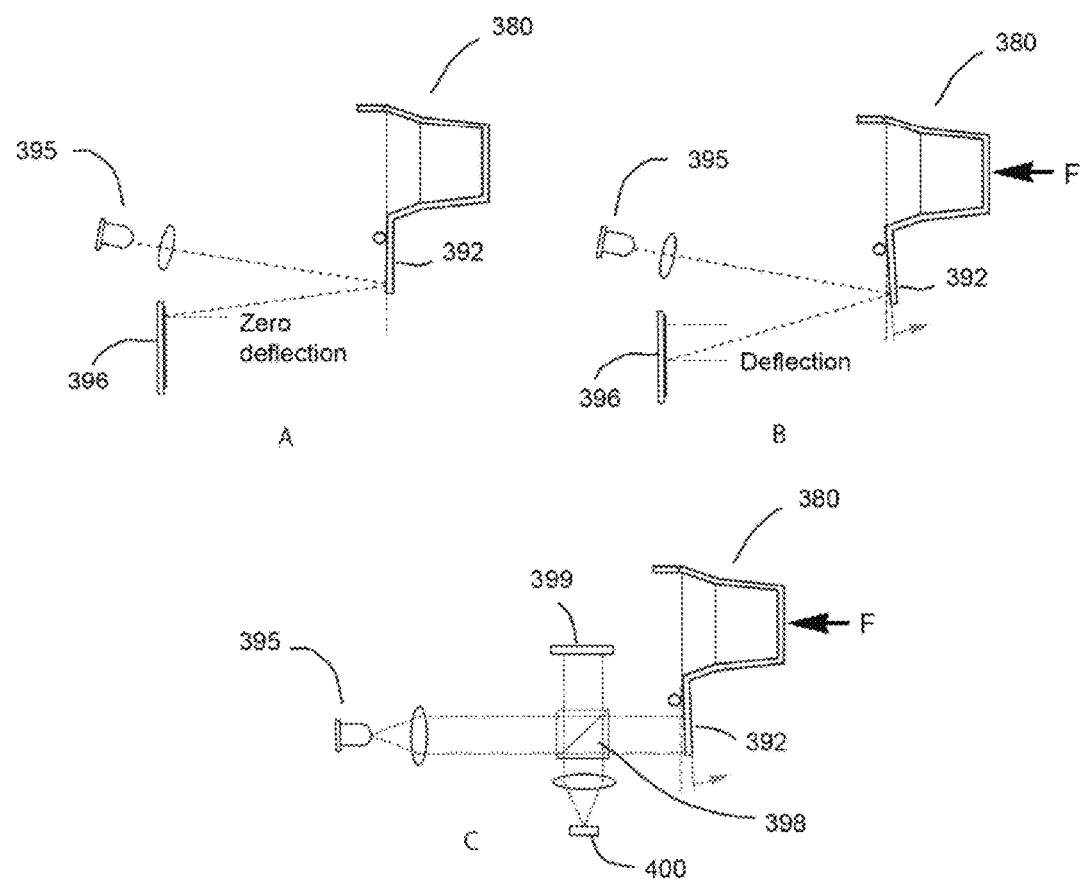
FIG. 16 depicts methods of determining the degree of deflection of a deflection tab

A user may measure the deflection of a reflective portion of the component that deflects during force application. This is shown in FIG. 16 and associated description. The user may measure radiation reflected from the reflective portion of the component and may also measure a change in radiation related to deflection of the reflective portion of the component. The user may (manually or even in an automated fashion) correlate a change in the reflected radiation to the force.

The methods may include application of the force through a contract surface that is flat, but the surface—as described elsewhere herein—may also be characterized as being concave. Suitable concave surfaces are described elsewhere herein; one such suitable surface may have a radius of curvature greater than about 7 mm, or even greater than about 8 mm.

In some applications of the disclosed methods, the osculated area of the ocular globe remains essentially constant during force application. As shown in FIG. 13B, the osculating surface of osculator 337 is adapted for cornea 320 such that the surface area of osculation remains virtually constant during a measurement cycle and fills osculator 337 immediately upon contact.

The methods may also include the use of a strain gauge of the component to estimate the force. As described elsewhere herein, a component may have a strain gauge disposed on the component, and deflection caused by applanation/osculation causes an elongation of the material of the strain gauge and a related measurable change in electrical resistance.

A user may also measure at least of one pupil latency, pupil constriction velocity, pupil dilation velocity, or any combination thereof. This may be accomplished by illuminating the retina of the subject with illumination sufficient to stimulate the retina and initiate the pupillary reflex, and measuring at least of one pupil latency, pupil constriction velocity, pupil dilation velocity, or any combination thereof. Pupillary measurements may be performed in a non-contact manner, e.g., the retina may be stimulated without a component also contacting the subject's ocular globe. In some embodiments, however, pupillary measurements may be performed while a component contacts the ocular globe.

The retinal stimulation may be provided by a fixation light. In some embodiments, the user may use a fixation light on which the subject focuses during method operation. The fixation light may be adapted to provide a stronger illumination when appropriate to stimulate the subject's retina and to allow the user to monitor the pupil's response to the stimulation. The user suitably images (e.g., via CCD, ultrasound, or other imager) the pupil's response to the stimulating illumination. The images may be collected and analyzed in real time. Alternatively, the images of the pupil may be recorded and then analyzed at a later time. A user may also stimulate the retina using an alternative source of illumination in addition to (or in place of) a fixation light.

The present disclosure also provides systems for measuring intracranial pressure in a subject. An exemplary system suitably includes an ophthalmic component having a having an osculating optical surface adapted to contact a subject's globe; and a force applicator.

As explained elsewhere herein, the force applicator may be a device (e.g., a screw drive or other component) that advances the component against the ocular globe of the subject. The force applicator may also be a device (e.g., a pump) that pressurizes the control volume of the component so as to exert a force against the subject's ocular globe.

Components suitable for use with the disclosed systems are described elsewhere herein. A component may feature a flat surface that osculates the ocular globe of the subject. A component may also feature an osculating optical surface of the ophthalmic component that is characterized as being concave. Such a surface may have a radius of curvature of at least about 7 mm.

An ophthalmic component may also be configured to engage an engagement region of the system. This engagement may be a tab-slot engagement (e.g., FIG. 15). The component may also be press-fitted to the engagement region, screwed to the engagement region, or otherwise engaged.

The disclosed systems may also include an imager. Suitable imagers (ultrasound devices, MRI, CT, cameras, video cameras, PMTs, and the like) are described elsewhere herein. An imager may be configured to be capable of imaging a subject's pupil, an intraocular blood vessel of the subject, or another part of a subject's ocular anatomy. Imagers are suitably configured to collect an image of the cornea, an intraocular blood vessel, the pupil, or any combination thereof. Video images may be analyzed using Eulearian Video Magnification ("Eulerian Video Magnification for Revealing Subtle Changes in the World" Frederic (Fredo) Durand, William T. Freeman, John V. Guttag, Michael Rubinstein, Eugene Inghaw Shih and Hao-Yu Wu; Massachusetts Institute of Technology for detection of ocular or peri-ocular blood vessel motion detection (e.g. collapse) or pupillary.

As described elsewhere herein, components may include a reflective portion. This portion may be a tab or other projection, and is suitably adapted to deflect when the osculating optical surface of the component is exerted against a subject's ocular globe. A system may also include a device configured to illuminate the reflective portion. Systems may further include a device (e.g., linear photo-detector, CCD or PMT) that is adapted to monitor radiation reflected from the reflective portion, or even adapted to monitor changes in radiation (e.g., change in radiation intensity, change in location of reflected radiation, or both) related to deflection of the reflective portion. A system may be further configured to correlate a change in radiation reflected from the reflective portion of the component to a force applied through the component.

As described elsewhere herein, a system may also include a source of illumination. This source of illumination may be, e.g., a fixation light on which a subject may focus during system operation. The source of illumination need not be a fixation light, and may even be used exclusively for retina stimulation. A system's source of illumination may be configured to stimulate the retina of the subject. A system may also be configured to measure at least one of pupil latency, pupil constriction velocity, pupil dilation velocity, or any combination thereof. As described above, this may be accomplished by imaging the pupil's response to pupillary stimulation.

Non-limiting FIG. 13 presents cross sections of various exemplary osculating caps and osculator surfaces. An osculating cap holds the osculating surface and affixes it to the distal end of an optical module or other component. Measuring IOP utilizing osculator caps 335 shown in FIGS. 12A, B and C is based on osculator force and area as previously described.

FIG. 13A shows an exemplary osculating cap with an interface described in FIG. 10D. The distal surface is planar and the proximal surface is centrally convex surrounded by a planar surface. As osculating cap 335 is advanced towards the eye, applanation area 334 (also shown in FIG. 14 as 337) increases and is used in combination with applanation force to determine IOP. The osculation force at an area of applanation equal to a diameter of 3.06 mm is used to calculate resting IOP. The force of applanation is directly related to the change in IOP (ΔIOP). The relationship between applanation force and area with resting IOP is well established (Goldmann). Experiments have demonstrated that force necessary to collapse the retinal vessels at applanation areas greater than Goldmann measurements (resting IOP measurements), are predictable and repeatable and range from 0-40 g. The degree of osculation cap displacement following initial corneal contact is typically less than about 1 mm to reach about 40 grams force, but may vary based upon the patients' anatomy and the selected osculating instruments.

Figure 20:
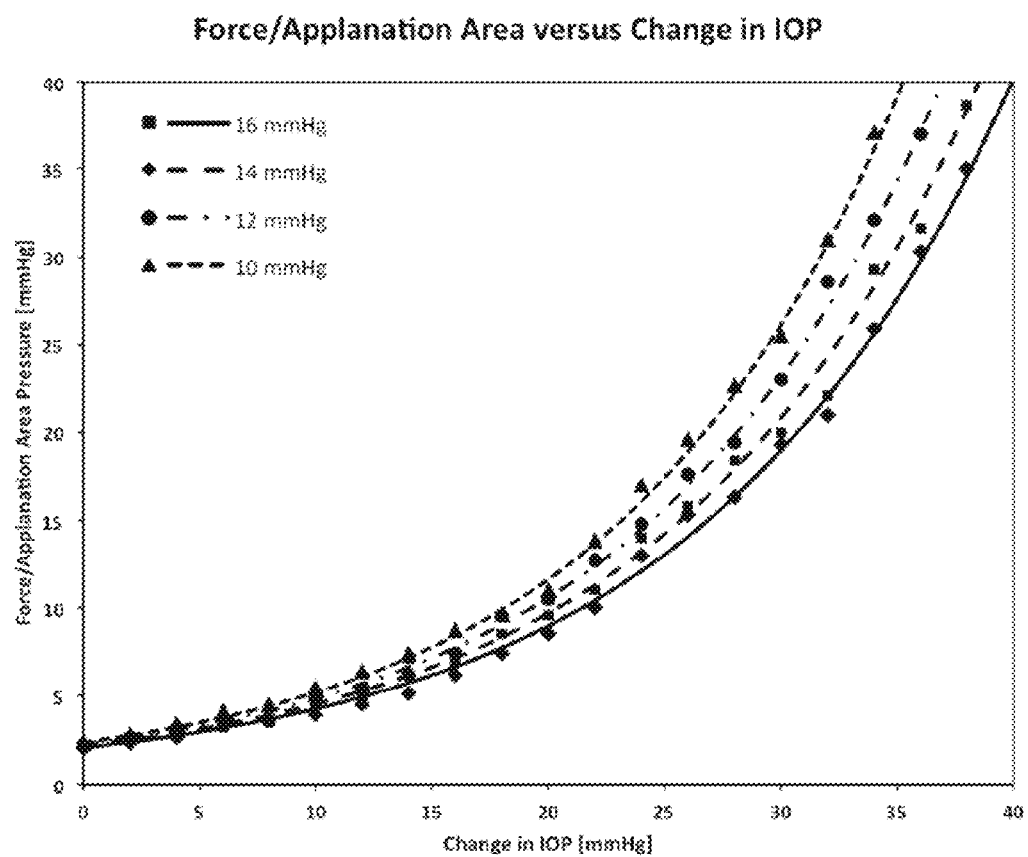
FIG. 20 shows representative experimental data and trend lines demonstrating the relationship between applanation force/area to ΔIOP for several different resting IOPs.

Before the present disclosure, there has been little need to explore changes in IOP with applanation areas substantively greater than 3.06 mm. However, a person of ordinary skill in the art can readily determine the correlation of ΔIOP to resting IOP, force, and applanation area. FIG. 20 shows representative experimental data and trend lines demonstrating the relationship between applanation force/area to ΔIOP for several different resting IOPs. The y-axis is force/applanation area and x-axis is the ΔIOP over resting IOP measured by a pressure transducer.

FIG. 13B shows alternative device that includes osculating cap 332 and non-deformable concave osculator 337. The radius of curvature of the osculator 337 is preferably greater than the radius of curvature of cornea 320. Cornea 320 may essentially fill the concavity of non-deformable osculator 337 that contacts the eye. The IOP increases when osculating cap 332 advances with an increasing force. Force can be measured using a wide variety of methods including—but not limited to—a force transducer embedded in the distal side of osculator 337, the back electro-motive force from a motor advancing the osculator or using indirect measurements of force as described herein. Osculating surface of osculator 337 is essentially matched or otherwise adapted for cornea 320 such that the surface area of osculation remains virtually constant during a measurement cycle and fills osculator 337 immediately upon contact. As a result of matching the osculating surface to the cornea, pressure of the eye is supported by the entire osculating surface, and readings for a force transducer embedded on the distal surface are directly related to IOP. A tonometer such as the Ziemer Pascal Dynamic Contour Tonometer (Ziemer USA, Inc. Alton, Ill.) is reasonably suitable for this purpose. The force can also be measured as described above in FIG. 13A, but because the osculation area is virtually constant during the entire measurement period, the osculation area need not be measured in order to determine ΔIOP.

Using a comparatively large osculating surface area increases the effective aperture for the retinal imaging and illumination paths over the applanating cap shown in FIG. 13A. Increasing the aperture can increase the effective field of view of the retina and increase illumination performance of the system. Osculator 337 diameter is preferably larger than or equal to the corneal diameter.

Another method of measuring force for purposes of determining IOP and ΔIOP at the osculating cap is shown in exemplary FIG. 13C. In that figure, osculating cap 332 comprises semi-rigid deformable osculator 338, control volume 345, and proximal port 348 connected to pressure transducer 350. For retinal imaging purposes semi-rigid osculator 338 must be optically clear and can be composed of a thin sheet (e.g., about 10 mils to about 60 mils) of flexible material. Optical materials such as optical aliphatic polyether polyurethane or clear polypropylene-based sheet are suitable. A suitable range of material properties for the surface are ultimate elongation of 200-1000%, 300% Modulus of 1.5-4.0 MPa, and ultimate tensile strength of 20-40 MPa. The semi-rigid deformable osculator 338 has a suitable pre-osculating radius of curvature greater than the curvature of the cornea (a radius may be greater than about 7 mm or about 8 mm). When the surface osculates the cornea, the osculating surface may slightly deform so as to match the cornea curvature. The eye fills osculator 338 so as to occupy the curved portion of control volume 345.

Before contact, control volume 345 is at steady-state and the pressure is set at a zero point. Upon contact, control volume 345 compresses, and pressure and force on the eye increase. The osculator 338 and cornea 320 deform after the osculator cap contacts the cornea, and the pressure in the control volume is measured with pressure transducer 350. Depending on the curvature and material properties of the osculator, when the eye is osculated the contact area can remain virtually constant or change during the measurement period. As the control volume changes due to deformation of the osculator, the pressure measurements will be directly related to the force on the eye and can be calibrated given the material properties of the osculating surface and the control volume pressure change. The IOP is calculated with previously described methods by using the force derived from the pressure change and the osculating area. An example of a suitable pressure transducer is a solid state piezoresistive pressure transducer (Omega PX170-07 DV) connected to port 348 open to the proximal surface of control volume 345. The pressure in the control volume can be continuously measured and advancement of the osculator will increase the pressure in the control volume and the eye.

FIG. 13D shows osculating cap 332 with an active pneumatic pressurization of deformable elastomeric osculator 339, which conforms to corneal curvature. When control volume 345 is pressurized by pump 349 and measured by transducer 350, the control volume pressure is directly proportional to the pressure in the eye. Control volume 345 can be suitable pressurized with a fluid, e.g., air, water, saline, or other liquid or gas and delivered to the control volume by a wide variety of mechanisms including a piston pump 349 actuated manually or electronically through a pump and computerized controller. The fluid may be delivered to the control volume via a conduit that places the control volume into fluid communication with a fluid reservoir (not shown). A fluid reservoir may be exterior to the osculator cap. As one such example, the system may include a squeeze bulb that allows the user—manually or via automation—to deliver fluid (e.g., air) to the control volume from the environment exterior to the cap. A suitable elastomeric osculator for retinal imaging purposes may be optically clear. A suitable cap may also comprise a thin film (e.g., 0.5-25 mils) of flexible material. Optical materials such as optical aliphatic polyether polyurethane or clear polypropylene-based films are suitable. A suitable range of material properties for the surface are ultimate elongation of 200-1000%, a 300% Modulus of 1.5-4.0 MPa, and an ultimate tensile strength of 20-40 MPa. The elastomeric osculator is suitably less rigid than the cornea of the eye so that the elastic surface at least partially osculates the eye when contacted to the cornea.

To determine the retinal vessel pressure, osculating cap 349 in FIG. 13D is first supported on the cornea such that osculator 339 conforms to the cornea, and does not exert a significant pressure over atmospheric pressure. This can be achieved by allowing the control volume pressure to equalize to atmospheric by venting to the atmosphere or reduction of pressure by suction. After the cornea is supported by the thin film osculator, the pressure in the control volume is increased until the retinal vessel collapses. Because the osculating interface 334 is in contact and supported by the cornea, the pressure in control volume 345 is proportionally equal to the IOP. For osculating cap 332 in FIG. 13D, resting IOP need not be determined for determination of ICP. Using osculating cap 332 also obviates the need to advance osculator cap 332 to increase IOP. It should be understood that a user may advance an osculator cap that comprises a pressurizable control volume and may even pressurize the control volume while advancing the cap, although this may not be necessary.

Figure 14:
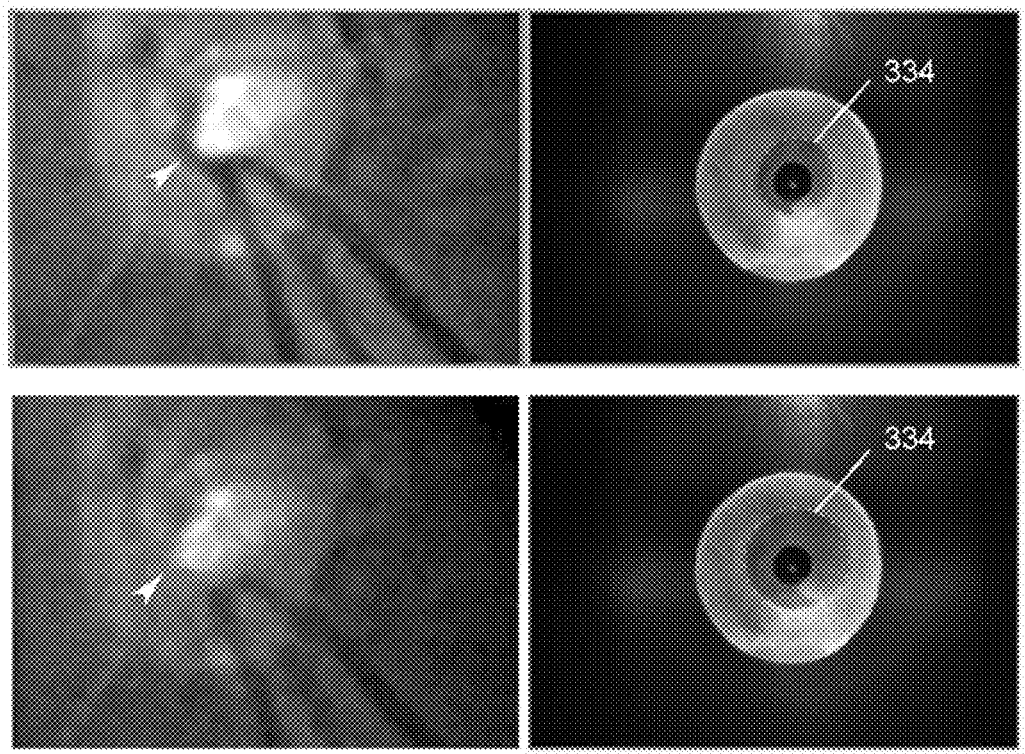
FIG. 14 depicts an image thru an osculating cap of the retina and the applanation area of the cornea before and after retinal vessel collapse

FIG. 14 shows representative images taken with the methods and apparatus described herein and shown in FIGS. 5, 6, 7, 8, 9, 10D, 13A and osculating cap 380 shown in FIGS. 15 and 17. FIG. 14 shows human retinal images of the optic disc (L) and cornea images of the osculation interface 334 (R). The top row of FIG. 14 shows retina 330 upon initial osculation and prior to CRV collapse. The arrows in FIG. 14 (L) show the location of CRV prior to (top) and post (lower) CRV collapse. The right images are representative of the cornea osculation area 337 prior to (upper) and post (lower) CRV collapse.

FIGS. 15 and 16 illustrate alternative, non-limiting methods of determining the contact force between the ocular globe and an instrument (e.g., an osculating cap) by measuring deflection of a portion of the osculating cap in response to osculation of the cornea.

In FIG. 15 osculating cap 380 via cap extension 378 engage with and are removably affixed to cap holder 390 permanently attached to the distal end of the optical train (not shown). FIG. 15A illustrates osculating cap 380 prior top engagement with cap holder 39 and FIG. 15B illustrated osculating cap 380 after engagement. Hinge 379 located on cap extension 378 allows rotation of the osculation cap 380 such that reflecting tab 392 presses onto rod 393 and causes a deflection in the position of the reflecting tab 392. Reflecting tab 392 is configured such that electromagnetic energy from light source and lens 395 is reflected or scattered from the proximal side of reflecting tab 392. Selection of the reflectivity, index of refraction or even surface finish are representative examples of the many ways to suitable reflect or scatter light from reflecting tab 392. Osculating cap 380 may be configured so that a small amount of rotation, preferably less than 1 degree, occurs in response to varying degrees of osculation force. This small rotation is configured to induce a deflection (which may be comparatively large) of reflecting tab 392 away from the cap holder 390. The magnitude of the deflection is dependent on the osculation force. One exemplary material for cap 380 and reflecting tab 392 is poly methyl methacrylate (PMMA). A force of 1 to 40 grams pressing on the cap can cause a range of deflections from 1 to 40 microns, depending on the thickness and width of the tab.

As shown in FIG. 16A and FIG. 16B, force F from the cornea directed against osculator cap 380 may result in the rotation of osculator cap 380, which in turn results in the deflection of reflecting tab 392 or other structure of the osculator cap as it is held in place. A dotted line (labeled with "Zero deflection") represents the position for the reflection tab 392, when zero force applied. Light source and lens 395 provides electromagnetic radiation (e.g., visible or infrared light from an LED, laser or other illumination source, ultrasound, and the like) directed onto and reflected from reflection tab 392 and collected by photodetector 396 or similarly appropriate electromagnetic sensor. The light source and lens 395 and photodetector 396—e.g., shown in FIG. 16A and FIG. 16B—may be configured such that contact with the cornea can result in changes in the light position, intensity or the like. Suitable electromagnetic energy by be reflected or scattered to induce a measureable change detectable by photosensor 396. By way of example only, a suitable photodetector is a TSL1401CL linear sensor array (AMS-TOAS, Inc. Plano, Tex.) used in conjunction with an LED emitting 400 nm to 1000 nm of light. When osculator cap 380 contacts the eye, reflection tab 392 is deflected and the position of light is sensed by photodetector 392. By selection of the physical characteristics of reflecting tab 392, the signal from photodetector 392 may be calibrated to indicate the force of osculation. Other means of measuring deflection can be used and may include contact devices such as a linear variable differential transformer (LVTD) or distributed impedance sensor technology (DIST) and non-contact devices such as a differential variable reluctance transducer (DVRT).

FIG. 16C shows an exemplary configuration of components to perform optical comparative flat interferometry using monochromatic collimated light and lens 395 and beam splitter 398 to image the interference fringe patterns generated by the reflection of light off of reference flat 399 and the deflected surface 392. Reference surface 399 can be placed either in line or orthogonal to the deflecting surface depending on geometrical constraints. By counting the number of interference bands (also called fringes) and deviation from zero deflection, one can determine a change in parallelism related to light source wavelength. The number of fringes corresponds to the degree of deflection (tilt) between the reference flat and the deflecting surface with a single fringe corresponding to the distance equal to the wavelength of the light source.

FIG. 17 shows a strain gauge pattern on an osculator to measure the force exerted on the cornea. A thin strain sensitive material 342 can be mounted on the proximal side of the osculator cap surface and used as a strain gauge to measure the deflection of the cap surface. In the example shown, a suitable material such as Mylar™ is bonded to the surface in a pattern such that a small deflection caused by applanation/osculation will cause an elongation of the material and a measurable change in electrical resistance.

Figure 18:
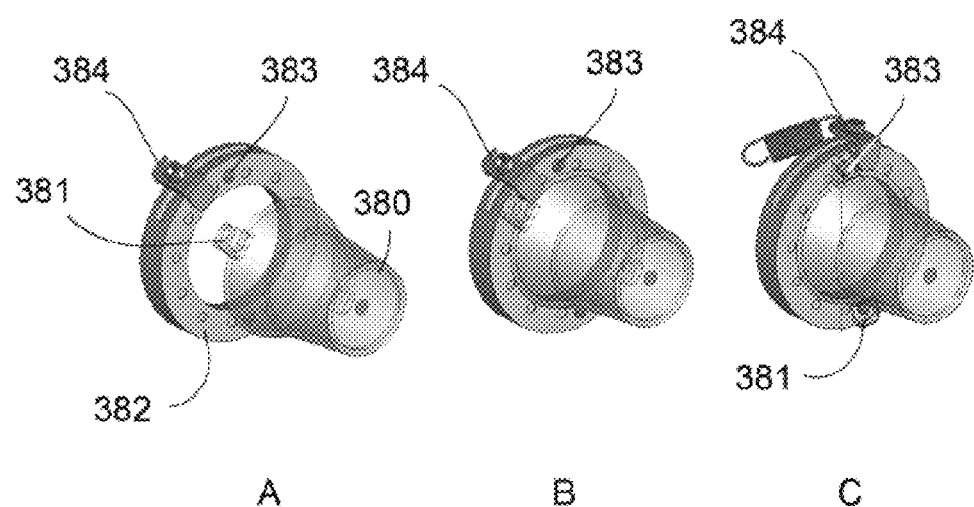
FIG. 18 depicts an exemplary scheme for removably attaching an osculating cap.

FIG. 18 illustrates a method to removably hold in place osculating cap 380. The osculating cap 380 has locking tabs 381 that are aligned to fit and engage a spring-loaded mechanism 382 actuating pin 383 which pierces tab 381, locking it in place. In this configuration, as osculation cap 380 is rotated clockwise and the tabs 381 pushes a cam 384 that compresses a spring-loaded pin so that the tab can engage the pin.

Optical elements in the present invention may be configured such that there may be imaging of optical structures from the cornea through the retina. As a result, images of the iris may also be collected and analyzed. This function is of value to the medical professional diagnosing brain injury. Pupillary reflex assessment is a fundamental part of the neurological examination. Changes in size and reactivity of the pupil to bright light stimuli can be a sign of neurological deterioration. In particular, the pupillary reflex can be analyzed to quantify clinically relevant variables including: (1) Latency—the time from the beginning of the light stimulus and the beginning of pupil constriction, (2) Constriction velocity—the velocity of pupil constriction measured as change in pupil area divided by time, and (3) Dilation velocity—the velocity of pupil dilation measured as change in pupil area divided by time.

Figure 19:
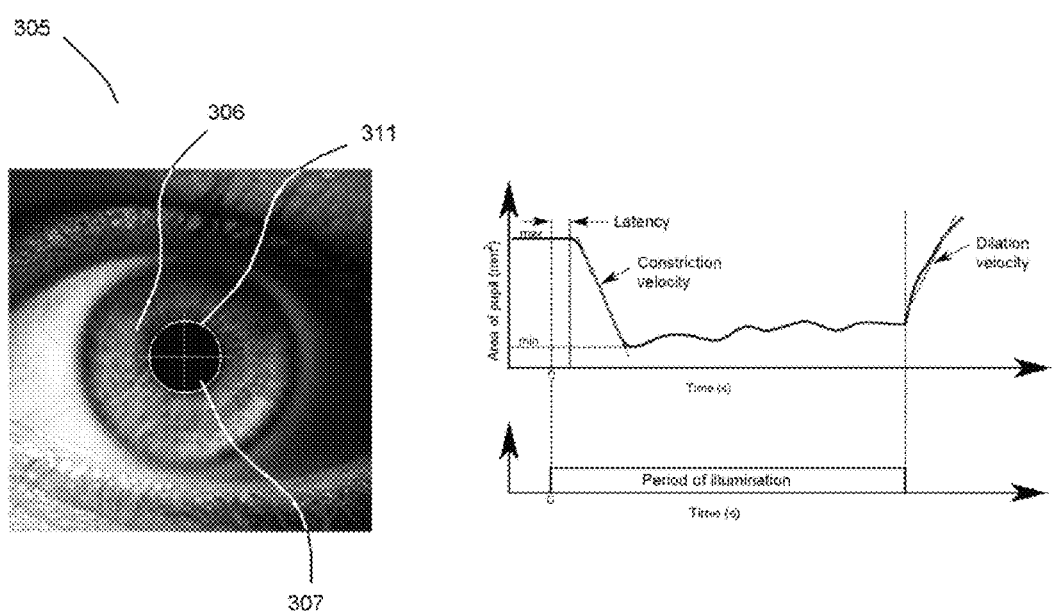
FIG. 19 depicts imaging and data analysis for pupillometry.

FIG. 19 presents a representative image of the human eye 305 from the ICP system with computer image analysis highlighting the pupil area 311. The right image shows two data streams collected by the ICP system to perform pupillometry and the relevant parameters for the medical professional. The lower stream shows the period of illumination from a bright light stimuli 310. The upper data stream shows the response of the pupil to bright light stimuli 310. In this plot, the y-axis shows the area of the pupil 311 against the x-axis showing time in seconds. The two plots are synchronized in time.

The disclosed systems, by using images, sensors, and processors (which may be independent of ICP measurement or be integrated into the ICP measurement process), data from the pupil can be easily obtained. This invention can illuminate the eye and initiate the pupillary reflex and recorded images (e.g., video) may be analyzed to quantify pupil latency, constriction velocity, and dilation velocity. Pupillometry can be performed during measurement of ICP. Further, it can be performed independent of ICP measurements.

Osculation of the ocular globe is not necessary for performing pupillometry. For example, osculation cap in FIG. 13B would not require osculation to image the pupil and perform pupillometry. The measurement of pupillary reflex is suitably performed on both left and right eyes as it can provide valuable information not only about brain injury but also about optic nerve or oculomotor nerve damage.

The disclosed technology has been shown and described with reference to exemplary drawings and not drawn to scale. It will be understood by one of skill in the art that various changes in detail may be effected without departing from the scope or spirit of the invention as defined by the claims.

What is claimed:

1. A method of estimating a pressure in a subject, comprising:
    with a component having an osculating surface that comprises a deformable material and that partially defines a closed control volume enclosed within an ophthalmic component, applying a force to the subject's cornea, sclera, eyelid, or any combination thereof with the osculating surface while the osculating surface contacts a portion of the subject's cornea, sclera, eyelid, or any combination thereof,
    the force being sufficient to collapse an intraocular blood vessel of the subject;
    visualizing the intraocular blood vessel through the component; and
    correlating the force that collapses the intraocular blood vessel to an estimated intracranial pressure of the subject.

2. The method of claim 1, wherein at least some of the force is applied by advancing the component.

3. The method of claim 1, wherein at least some of the force is applied by increasing a pressure within the control volume of the component so as to exert the osculating surface toward the subject's cornea, sclera, eyelid, or any combination thereof.

4. The method of claim 3, wherein the pressure is increased in an automated fashion.

5. The method of claim 1, wherein the correlating is performed by a processor configured to estimate intracranial pressure of the subject based on one or more images of the intraocular blood vessel of the subject's eye.

* * * * *